(12) United States Patent
Hudziak et al.

(10) Patent No.: US 6,399,063 B1
(45) Date of Patent: *Jun. 4, 2002

(54) MONOCLONAL ANTIBODIES DIRECTED TO THE HER2 RECEPTOR

(75) Inventors: Robert M. Hudziak, Corvallis, OR (US); H. Michael Shepard, Rancho Santa Fe, CA (US); Axel Ullrich, Portola Valley, CA (US); Brian M. Fendly, Half Moon Bay, CA (US)

(73) Assignee: Genentech, Inc., South San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/152,654

(22) Filed: Sep. 14, 1998

Related U.S. Application Data

(63) Continuation of application No. 09/044,197, filed on Mar. 17, 1998, now Pat. No. 6,165,464, which is a continuation of application No. 08/447,478, filed on May 23, 1995, now Pat. No. 5,772,997, which is a continuation of application No. 08/286,303, filed on Aug. 5, 1994, now Pat. No. 5,677,171, which is a continuation of application No. 07/977,453, filed on Nov. 18, 1992, now abandoned, which is a continuation of application No. 07/147,461, filed on Jan. 25, 1988, now abandoned, which is a continuation-in-part of application No. 07/143,912, filed on Jan. 12, 1988, now abandoned.

(51) Int. Cl.$^7$ .................. A61K 39/395; A61K 39/00; C07K 16/30; C07K 16/46; C12P 21/08

(52) U.S. Cl. .................. 424/138.1; 424/133.1; 424/134.1; 424/130.1; 424/141.1; 424/142.1; 424/143.1; 424/155.1; 424/156.1; 424/174.1; 424/277.1; 424/85.1; 530/387.3; 530/387.7; 530/388.8; 530/388.22

(58) Field of Search .................. 424/134.1, 133.1, 424/130.1, 142.1, 143.1, 155.1, 156.1, 174, 85.1, 277.1, 138.1, 141.1; 530/387.7, 388.22, 388.8, 387.3

(56) References Cited

U.S. PATENT DOCUMENTS

| | | |
|---|---|---|
| 4,699,877 A | 10/1987 | Cline et al. |
| 4,753,894 A | 6/1988 | Frankel et al. |
| 4,906,646 A | 3/1990 | Honn et al. |
| 4,935,341 A | 6/1990 | Bargmann et al. |
| 4,943,533 A | 7/1990 | Mendelsohn et al. |
| 4,957,735 A | 9/1990 | Huang |
| 4,963,354 A | 10/1990 | Shepard et al. |
| 4,968,603 A | 11/1990 | Slamon et al. |
| 5,108,934 A | 4/1992 | Rokugawa et al. |
| 5,169,774 A | 12/1992 | Frankel et al. |
| 5,288,477 A | 2/1994 | Bacus |
| 5,308,626 A | 5/1994 | Landucci et al. |
| 5,401,638 A | 3/1995 | Carney et al. |
| 5,470,571 A | 11/1995 | Herlyn et al. |
| 5,604,107 A | 2/1997 | Carney et al. |
| 5,677,171 A | 10/1997 | Hudziak et al. |
| 5,720,937 A | 2/1998 | Hudziak et al. |
| 5,720,954 A | 2/1998 | Hudziak et al. |
| 5,725,856 A | 3/1998 | Hudziak et al. |
| 5,747,261 A | 5/1998 | King et al. |
| 5,770,195 A | 6/1998 | Hudziak et al. |
| 5,772,997 A | 6/1998 | Hudziak et al. |
| 5,824,311 A | 10/1998 | Green et al. |
| 5,977,322 A | 11/1999 | Marks et al. |
| 5,985,553 A | 11/1999 | King et al. |

(List continued on next page.)

FOREIGN PATENT DOCUMENTS

| | | |
|---|---|---|
| EP | 118365 | 9/1984 |
| EP | 359282 A2 | 3/1990 |
| EP | 239400 | 8/1994 |
| EP | 616812 | 9/1994 |
| EP | 667165 A1 | 8/1995 |

(List continued on next page.)

OTHER PUBLICATIONS

U.S. application No. 06/836,414, King, filed May 3, 1986.
"Genentech Herceptin recommended for use with Taxol as first–line therapy, but not for use in combination with anthracyline chemotherapy—ODAC." *Daily Ink* pp. 1–2 (Sep. 4, 1998).
Aboud–Pirak et al., "Efficacy of Antibodies to Epidermal Growth Factor Receptor Against KB Carcinoma In Vitro and in Nude Mice" *Journal of the National Cancer Institute* 80(20):1605–1611 (Dec. 21, 1988).
Akiyama et al., "Potentation of Cytotoxic Activity of Immunotoxins on Cultured Human Cells" *Cancer Research* 45:1005–1007 (1985).
Akiyama et al., "The product of the human c–erbB–2 Gene: a 185–Kilodalton Glycoprotein with tyrosine Kinase Activity" *Science* 232:1644–1646 (1986).
Arteaga et al., "Antibodies Against p185/HER2 Enhance Etoposide–Induced Cytotoxicity Against Human Breast Carcinoma Cells" *Proceedings of ASCO–29th Annual Meeting* (Abstract #101), Orlando FL 12:75 (1993).
Ballet et al., "Evaluation of a "Nude" Mouse–Human Tumor Panel as a Predictive Secondary Screen for Cancer Chemotherapeutic Agenst" *J. Natl. Canc. Inst* 63(5):1185–1188 (1979).
Bargmann et al., "Multiple Independent Activations of the neu Oncogene by a Point Mutation Altering the Transmembrane Domain of p185" *Cell* 45:649–659 (Jun. 6, 1986).

(List continued on next page.)

Primary Examiner—Geetha P. Bansal
(74) Attorney, Agent, or Firm—Wendy M. Lee

(57) ABSTRACT

A method of inhibiting growth of tumor cells which overexpress a growth factor receptor or growth factor by treatment of the cells with antibodies which inhibit the growth factor receptor function, is disclosed. A method of treating tumor cells with antibodies which inhibit growth factor receptor function, and with cytotoxic factor(s) such as tumor necrosis factor, is also disclosed. By inhibiting growth factor receptor functions tumor cells are rendered more susceptible to cytotoxic factors.

18 Claims, 6 Drawing Sheets

U.S. PATENT DOCUMENTS

| | | | |
|---|---|---|---|
| 6,015,567 | A | 1/2000 | Hudziak et al. |
| 6,054,561 | A | 4/2000 | Ring |
| 6,123,939 | A | 9/2000 | Shawver et al. |
| 6,156,321 | A | 12/2000 | Thorpe et al. |
| 6,165,464 | A | 12/2000 | Hudziak et al. |
| 6,217,866 | B1 | 4/2001 | Schlessinger et al. |

FOREIGN PATENT DOCUMENTS

| | | |
|---|---|---|
| JP | 60-243027 | 12/1985 |
| JP | 62-108157 | 5/1987 |
| WO | WO 85/03357 | 8/1985 |
| WO | WO 87/07646 | 12/1987 |
| WO | WO 89/10412 | 11/1989 |
| WO | WO 91/02062 | 2/1991 |
| WO | WO 94/22478 | 10/1994 |

OTHER PUBLICATIONS

Bargmann et al., "The neu Oncogene Encodes an Epidermal Growth Factor Receptor–related Protein" *Nature* 319:226–230 (Jan. 16, 1986).

Baselga et al., "Anti Her2 Humanized Monoclonal Antibody (MAb) Alone and in Combination with Chemotherapy Against Human Breast Carcinoma Xenografts" *Proceedings of ASCO–13th Annual Meeting* (Abstract #53), Dallas, TX 13:63 (1994).

Baselga et al., "Phase II Study of Weekly Intravenous Recombinant Humanized Anti–p185/HER2 Monoclonal Antibody in Patients With HER2/neu–Overexpressing Metastatic Breast Cancer" *J. Clin. Oncol.* 14(3):737–744 (1996).

Baselga et al., "Receptor Blockade With Monoclonal Antibodies as Anti–Cancer Therapy" *Pharmac. Ther.* 64:127–154 (1994).

Beguinot et al., "Down–Regulation of the Epidermal Growth Factor Receptor in KB Cells is Due to Receptor Internalization and Subsequent Degradation in Lysozymes" *Proc. Natl. Acad. Sci. USA* 81(8):2384–2388 (1984).

Bernards et al., "Effective Tumor Immunotherapy Directed Against an Oncogene–encoded Product Using a Vaccinia Virus Vector" *Proc. Natl. Acad. Sci. USA* 84:6854–6858 (Oct. 1987).

Bjorn et al., "Evaluation of Monoclonal Antibodies for the Development of Breast Cancer Immunotoxins" *Cancer Research* 45:1214–1221 (1985).

Bucholtz, J. D., "Radiolabeled Antibody Therapy" *Semin. Oncol. Nurs.* (abstract only) 3(1):67–73 (1987).

Cole et al., "The EBV–Hybridoma Technique and Its Application to Human Lung Cancer" *Monoclonal Antibodies and Cancer Therapy,* Reisfeld et al., New York:Alan R. Liss, Inc. pp. 77–96 (1985).

Coussens et al., "Tyrosine Kinase Receptor with Extensive Homology to EGF Receptor Shares Chromosomal Location with neu Oncogene" *Science* 230:1132–1139 (1985).

De Santes et al., "Radiolabeled Antibody Targeting of the HER–2/neu Oncoprotein–1" *Cancer Research* 52:1916–1923 (1992).

Douillard et al., "Radioimmunotection of Human Tumors with Radiolabeled Monoclonal Antibodies" *Oncogenes to Tumor Antigens,* Geraldo et al. (eds.), Elsevier Sci. Publ. (1985).

Drebin et al., "Development of Monoclonal Antibodies Reactive with the Product of the neu Oncogene" *Symposium on Fundamental Cancer Research* 38: 277–289 (1986).

Drebin et al., "Down–Modulation of an Oncogene Protein Product an Reversion of the Transformed Phenotype by Monoclonal Antobodies" *Cell* 41(3): 695–706 (1985).

Drebin et al., "Inhibition of tumor growth by a monoclonal antibody reactive with an oncogene–encoded tumor antigen" *Proc. Natl. Acad. Sci.* 83:9129–9133 (1986).

Drebin et al., "Monoclonal Antibodies Identify a Cell–surface Antigen Associated with an Activated Cellular Oncogene" *Nature* 312:545–548 (Dec. 6, 1984).

Drebin et al., "Monoclonal antibodies reactive with distinct domains of the neu oncogene–encoded p185 molecule exert synergistic anti–tumor effects in vivo" *Oncogene* 2:273–277 (1988).

Drebin et al., "Monoclonal Antibodies Specific for the neu Oncogene Product Directly Mediate Anti–tumor Effects In Vivo" *Oncogene* 2(4):387–394 (1988).

Fendly et al., "Characterization of Murine Monoclonal Antibodies Reactive to Either the Human Epidermal Growth Factor Receptor or HER2/neu Gene Product" *Cancer Research* 50:1550–1558 (Mar. 1, 1990).

Frankel et al., "Tissue Distribution of Breast Cancer –Associated Antigens Defined by Monoclonal Antibodies" *Journal of Biological Response Modifers* 4:273–286 (1985).

Fukushige et al., "Localization of a Novel v–erbB–Related Gene, c–erbB–2, on Human Chromosomes 17 and its Amplification in a Gastric Cancer Cell Line" *Molecular & Cellular Biology* 6(3):955–58 (1986).

Gill et al., "Monoclonal Anti–epidermal Growth Factor Receptor Antibodies Which are Inhibitors of Epidermal Growth Factor Binding and Antagonists of Epidermal Growth Factor–stimulated Tyrosine Kinase Activity" *Journal of Biological Chemistry* 259:7755–60 (1984).

Glassy et al., "Genetically Stable Human Hybridomas Secreting Tumor–Reactive Human Monoclonal IgM" *Cancer Investigation* 5:449–457 (1987).

Hancock et al., "A Monoclonal Antibody Against the c–erbB–2 Protein Enhances the Cytotoxicity of cis–Diamminedichloroplatinum Against Human Breast and Ovarian Tumor Cell Lines" *Cancer Research* 51:4575–4580 (Sep. 1, 1991).

Hudziak et al., "Amplified Expression of the HER2/ERBB2 Oncogene Induces Resistance to Tumor Necrosis Factor α in NIH 3T3 Cells" *Proc. Natl. Acad. Sci. USA* 85:5102–5106 (1988).

Hudziak et al., "Increased expression of the putative growth factor receptor p185$^{HER2}$ causes transformation and tumorigenesis of NIH 3T3 cells" *Proc. Natl. Acad. Sci.* 84:7159–7163 (1987).

Hudziak et al., "p185$^{HER2}$ Monoclonal Antibody Has Antiproliferative Effects In Vitro and Sensitizes Human Breast Tumor Cells to Tumor Necrosis Factor" *Molecular & Cellular Biology* 9(3): 1165–1172 (1989).

Katano et al., "Human Monoclonal Antibody to a Neuroectodermal Tumor Antigen (OFA–I–2)a" *Annals of New York Academy of Sciences*0077–8923:427–434 (1983).

King et al., "Amplification of a Novel v–erbB–Related Gene in a Human Mammary Carcinoma" *Science* 229:974–976 (1985).

Kipps et al., "Schemata for the production of monoclonal antibody–producing hybridomas" *Handbook of Experimental Immunology,* Herzenberg et al. (eds.), Blackwell Sci., Chapter 108, pp. 108.1–108.9 (1986).

Kokai et al., "Stage-and tissue-specific expression of the neu oncogene in rat development" *Proc. Natl. Acad. Sci USA* 84:8498–8501 (Dec. 1987).

Kraus et al., "Overexpression of the EGF Receptor–related Proto–Oncogene erbB–2 in Human Mammary Tumor Vell Lines by Different Molecular Mechanisms" *EMBO Journal* 6(3):605–610 (1987).

Krolick et al., "Specific Killing of a Human Breast Carcinoma Cell Line by a Monoclonal Antibody Coupled to the A–Chain of Ricin" *Cancer Immunol Immunother* 12:39–41 (1981).

Lewis et al., "Differential Responses of Human Tumor Cell Lines to Anti–p185$^{HER2}$ Monoclonal Antibodies" *Cancer Immunol. Immunother.* 37:255–263 (1993).

Loop et al., "Two Human Tumor–Associated Antigens, p155 and p210, Detected by Monoclonal Antibidoes" *Int. J. Cancer* 27:775–781 (1981).

Lupu et al., "Direct interaction of a ligand for the erbB2 oncogene product with the EGF receptor and p185$^{erbB2}$" *Science* 249:1552–1555 (1990).

Lyall et al., "EGF Induces Receptor Down–regulation with No Receptor Recycling in KB Cells" *J. Cell Physiol* 122(1):166–170 (1985).

Mansi et al., "In vivo Evaluation of an Anti–Melanoma Antibody, F(ab')2, Labelled with TC–99m" *Oncogenes to Tumor Antigens,* Geraldo et al., eds., Elsevier Sci. Publ. (1985).

Masui et al., "Mechanism of Antitumor Activity in Mice for Anti–Epidermal Growth Factor Receptor Monoclonal Antibodies with Different Isotypes" *Cancer Research* 46:5592–5598 (1986).

Masuko et al., "A murine Monoclonal Antibody That Recognizes an Extracellular Domain of the Human c–erbB–2 Protooncogene Product" *Jpn J. Cancer Res.* 80:10–14 (Jan. 1989).

McKenzie et al., "Generation and characterization of monoclonal antibodies specific for the human neu oncogene product, p185" *Oncogene* 4:543–548 (1989).

Morrison, S. L., "Transfectomas Provide Novel Chimeric Antibodies" *Science* 229:1202–1207 (Sep. 20, 1985).

Muller et al., "Single–Step Induction of Mammary Adenocarcinoma in Transgenic Mice Bearing the Activated c–neu Oncogene" *Cell* 54:105–115 (1988).

Munro, "Uses of chimaeric antibodies" *Nature* 312:597 (1984).

Myers et al., "Biological Effects of Monoclonal Antireceptor Antibodies Reactive with neu Oncogene Product, p185$^{neu}$" *Methods in Enzymology* 198:277–290 (1991).

Oi et al., "Chimeric Antibodies" *BioTechniques* 4(3): 214–221 (1986).

Osborne, Randall, "Full Approval of Breast Cancer Drug Expected by Year's End, FDA Panel OKs Genetech's Herceptin" *Daily Ink* pp. 1–2 (Sep. 4, 1998).

Padhy et al., "Identification of a Phosphoprotein Specifically Induced by the Transforming DNA of Rat Neuroblastomas" *Cell* 28:865–871 (1982).

Park et al., "Development of anti–p185$^{HER2}$ Immunoliposomes for Cancer Therapy" *Proc. Natl. Acad. Sci. USA* 92:1327–1331 (Feb. 1995).

Pegram et al., "Monoclonal Antibody to HER–2/neu Gene Product Potentiates Cytotoxicity of Carboplatin and Doxorubicin in Human Breast Tumor Cells" *Proceedings of the American Assoc. for Cancer Research* (Abstract # 2639–83rd Annual Meeting), San Diego, CA 33:442 (1992).

Pegram et al., "Phase II Study of Intravenous Recombinant Humanized Anti–p185 Monoclonal" *Proceedings of the ASCO–31st Annual Meeting* (Abstract #124), Los Angeles, CA 14:106 (1995).

Pennica et al., "Human Tumour Necrosis Factor: Precursor Structure, Expression and Homology to Lymphotoxin" *Nature* 312:724–729 (1984).

Pietras et al., "Antibody to HER–2/neu Receptor Blocks DNA Repair After Cisplatin in Human Breast and Ovarian Cancer Cells" *Oncogene* 9:1829–1838 (1994).

Pizza et al., "In Vitro Production of Human Antibodies Against Bladder Cancer" *Journal of Experimental Pathology* 4:335–346 (1987).

Ring et al., "Distribution and Physical Properties of BCA200, a Mr 200,000 Glycoprotein Selectively [C [C [C [D [D [3–[3– Sel protein Selectively Associated with Human Breast Cancer" *Cancer Research* 49:3070–3080 (1989).

Ring et al., "Identity of BCA200 and c–erbB–2 Indicated by Reactivity of Monoclonal Antibodies with Recombinant c–erbB–2" *Molecular Immunology* 28(8):915–917 (1991).

Rodeck et al., "Interactions between growth factor receptors and corresponding monoclonal antibodies in human tumors" *J. Cellular Biochem.* 35(4):315–320 (1987).

Rodeck et al., "Tumor Growth Modulation by a Monoclonal Antibody to the Epidermal Growth Factor Receptor: Immunologically Mediated and Effector Cell–independent Effects" *Cancer Research* 47(14):3692–3696 (1987).

Rosenthal et al., "Expression in Rat Fibroblasts of a Human Transforming Growth Factor–α cDNA Results in Transformation" *Cell* 46:301–309 (1986).

Sarup, "Characterization of an Anti–P185$^{her2}$ Monoclonal Antibody that Stimulates Receptor Function and Inhibits Tumor Cell Growth" *Growth Regulation* 1:72–82 (1991).

Sato et al., "Biological Effects in Vitro of Monoclonal Antibodies to Human Epidermal Growth Factor Receptors" *Mol. Biol. Med.* 1:511–529 (1983).

Schechter et al., "The neu Gene: An erbB–Homologous Gene Distinct from and Unlinked to the Gene Encoding the EGF Receptor" *Science* 229:976–978 (1985).

Schecter et al., "The neu oncogene: an erb–B–related gene encoding a 185,000–Mr tumour antigen" *Nature* 312:513–516 (1984).

Schlom et al., "Basic Principles and Applications of Monoclonal Antibodies on the Management of Carcinomas: The Richard and Hinda Rosenthal Foundation Award Lecture" *Cancer Resesearch* 46:3225–3238 (1986).

Semba et al., "A v–erbB–related protooncogene c–erbB–2, is distinct from the c–erb–B–1/epidermal growth factor–receptor gene and is amplified in a human salivary gland adenocarcinoma" *Proc. Natl. Acad. Sci. USA* 82:6497–6501 (1985).

Shepard et al., "Monoclonal Antibody Therapy of Human Cancer: Taking the HER2 Protooncogene to the Clinic" *J. Clin. Immunol.* 11(3):117–127 (1991).

Slamon et al., "Human Breast Cancer: Correlation of Relapse and Survival with Amplification of the HER–2/neu Oncogene" *Science* 235:177–182 (1987).

Smith et al., "Generation of human monoclona antibodies to cancer–associated antigens using limited numbers of patient lymphocytes" *Journal of Immunological Methods* 105:263–273 (1987).

Sobol et al., "Epidermal Growth Factor Receptor Expression in Human Lung Carcinomas Defined by a Monoclonal Antibody" *J. Natl. Cancer Institute* 79(3):403–407 (1987).

Sugarman et al., "Effects of Growth Factors on the Antiproliferative Activity of Tumor Necrosis Factor" *Cancer Research* 47:780–786 (1987).

Sugarman et al., "Recombinant Human Tumor Necrosis Factor–α: Effects on Proliferation of Normal and Transformed Cells in Vitro" *Science* 230:943–945 (1985).

Taetle et al., "Effects of Anti–Epidermal Growth Factor (EGF) Receptor Antibodies and an Anti EGF Receptor Rocombinant–ricin A Chain Immunoconjugate on Growth of Human Cells" *J. Natl. Cancer Institute* 80(13):1053–1059 (1988).

Takahashi et al., "Radioimmunodetection of Human Glioma Xenografts by Monoclonal Antibody to Epidermal Growth Factor Receptor" *Cancer Reserch* 47:3847–3850 (1987).

Tal et al., "Sporadic Amplification of the Her2/neu Protooncogene in Adenocarinomas of Various Tissues" *Cancer Research* 48:1517–1520 (Mar. 15, 1988).

Urban et al., "Tumor Necrosis Factor: A Potent Effector Molecule for Tumor Cell Killing by Activated Macrophages" *Proc. Natl. Acad. Sci. USA* 83:5233–5237 (Jul. 1986).

Van de Vijver et al., "Amplification of the neu (c–erbB–2) Oncogene in Human Mammary Tumors Is Relatively Frequent and Is Often Accompanied by Amplification of the Linked c–erbA Oncogene" *Molecular & Cellular Biology* 7(5):2019–2023 (1987).

van de Vijver et al., "Immunohistochemical detection of the neu protein in tissue sections of human breast tumors with amplified neu DNA" *Oncogene* 2:175–178 (1988).

Venter et al., "Overexpression of the c–erbB–2 Oncoprotein in Human Breast Carcinomas: Immunohistological Assessment Correlates with Gene Amplification" *Lancet* pp. 69–72 (1987).

Vitetta et al., "Redesigning Nature's Poisons to Create Anti–tumor Reagents" *Science* 238:1098–1104 (1987).

Vollmar et al., "Toxicity of Ligand and Antibody–Directed Ricin A–Chain Conjugates Recognizing the Epidermal Growth Factor Receptor" *J. Cellular Physiology* 131:418–425 (1987).

Weber et al., "Production of an Epidermal Growth Factor Receptor–Related Protein" *Science* 224:294–297 (Apr. 20, 1984).

Yamamoto et al., "Similarity of protein encoded by the human c–erb–B–2 gene to epidermal growth factor receptor" *Nature* 319:230–34 (1986).

Yokota et al., "Genetic Alterations of the c–erbB–2 Oncogene Occur Frequently in Tubular Adenocarinoma of the Stomach and Are Often Accompanied by Amplification of the v–erbA Homologue" *Oncogene* 2:283–287 (1988).

Zhou et al., "Association of Multiple Copies of the c–erbB–2 Oncogene with Spread of Breast Cancer" *Cancer Research* 47:6123–6125 (Nov. 15, 1987).

Katsumata et al., "Prevention of breast tumour development in vivo by downregulation of the p185 neu receptor" *Nature Medicine* 1:644–648 (1995).

Katsumata et al., "Prevention of breast tumor development in vivo by downregulation of the p185 neu receptor" *Nature Medicine* 1:644–648 (1995).

Goding *Monoclonal Antibodies: Principles and Practice*, 2nd edition, Academic Press pp. 11, 125–126 (1986).

Reddel et al., "Differential sensitivity of human breast cancer cell lines to the growth–inhibitory effects of tamoxifen" *Cancer Research* 45(4):1525–1531 (Apr. 1985).

Zhang et al., "Shared antigenic epitopes and pathobiological functions of anti–p185$^{her2/neu}$ monoclonal antibodies" *Experimental and Molecular Pathology* 67:15–25 (1999).

U.S. application No. 09/158,899, Greene et al., filed Sep. 23, 1998.

DiFiore et al., "erbB–2 is a potent oncogene when overexpressed in NIH/3T3 cells" *Science* 237(4811):178–182 (Jul. 10, 1987).

Disis et al., "Existent T–Cell and Antibody Immunity to HER–2/neu Protein in Patients with Breast Cancer" *Cancer Research* 54:16–20 (Jan. 1, 1994).

"Herceptin (Trastuzumab)" (Product Information) (1998).

Holtz, Andrew, "Herceptin: An Entirely New Weapon Against Cancer" *Exclusive Report from the 1998 ASCO Meeting* (1998).

Press et al., "Expression of the HER–2/neu proto–oncogene in normal human adult and fetal tissue" *Oncogene* 5:953–962 (1990).

Stedman *Medical Dictionary* 25th Edition: 1606.

Kern et al., "Inhibition of human lung cancer line growth by an anti–p185HER2 antibody" *American Journal of Respiratory Cell & Molecular Biology* 9(4):448–454 (Oct. 1993).

Ohnishi et al., "Prolonged survival of mice with human gastric cancer treated with an anti–c–ErbB–2 monoclonal antibody" *British Journal of Cancer* 71(5):969–973 (May 1995).

Tokuda et al., "In vitro and in vivo anti–tumour effects of a humanised monoclonal antibody against c–erbB–2 product" *British Journal of Cancer* 73(11):1362–1365 (Jun. 1996).

Letter dated May 4, 1999 from Louis Berneman of the University of Pennsylvania to Anna Hall of Genentech re: US Patent No. 5,824,311.

Bergers and Coussens, "Extrinsic regulators of epithelial tumor progression: metalloproteinases" *Current Opinion in Genetics & Development* 10(1):120–127 (Feb. 2000).

Bodey et al., "Failure of cancer vaccines: the significant limitations of this approach to immunotherapy" *Anticancer Research* 20(4):2665–2676 (Jul.–Aug. 2000).

Curti, B., "Physical barriers to drug delivery in tumors" *Critical Reviews in Oncology–Hematology* 14(1):29–39 (Feb. 1993).

"Declaration of Dr. Mark I. Greene dated Jun. 22, 2000 with Exhibits A, B and C".

DeNardo et al., "Strategies for developing effective radioimmunotherapy for solid tumors" *Clinical Cancer Research* 5(10 Suppl):3219s–3223s (Oct. 1999).

Epenetos et al., "Antibody guided irradiation of brain glioma by arterial infusion of radioactive monoclonal antibody against epidermal growth factor receptor and blood group A antigen" *British Medical Journal* 290(6480):1463–1466 (May 18, 1985).

Gura, T., "Systems for identifying new drugs are often faulty" *Science* 278(5340):1041–1042 (Nov. 7, 1997).

Hung et al., "Molecular cloning of the neu gene: Absence of gross structural alteration in oncogenic alleles" *Proc. Natl. Acad. Sci. USA* 83:261–264 (1986).

Jain, R., "Barriers to drug delivery in solid tumors" *Scientific American* 271(1):58–65 (Jul. 1994).

Stancovski et al., "Mechanistic aspects of the opposing effects of monoclonal antibodies to the ERBB2 receptor on tumor growth" *Proc. Natl. Acad. Sci. USA* 88(19):8691–8695 (Oct. 1, 1991).

Strobel and Cannistra, "β1–integrins partly mediate binding of ovarian cancer cells to peritoneal mesothelium in vitro" *Gynecologic Oncology* 73(3):362–367 (Jun. 1999).

Vitetta and Uhr, "Monoclonal Antibodies as Agonists: An Expanded Role for Their Use in Cancer Therapy" *Cancer Research* 54(20):5301–5309 (Oct. 15, 1994).

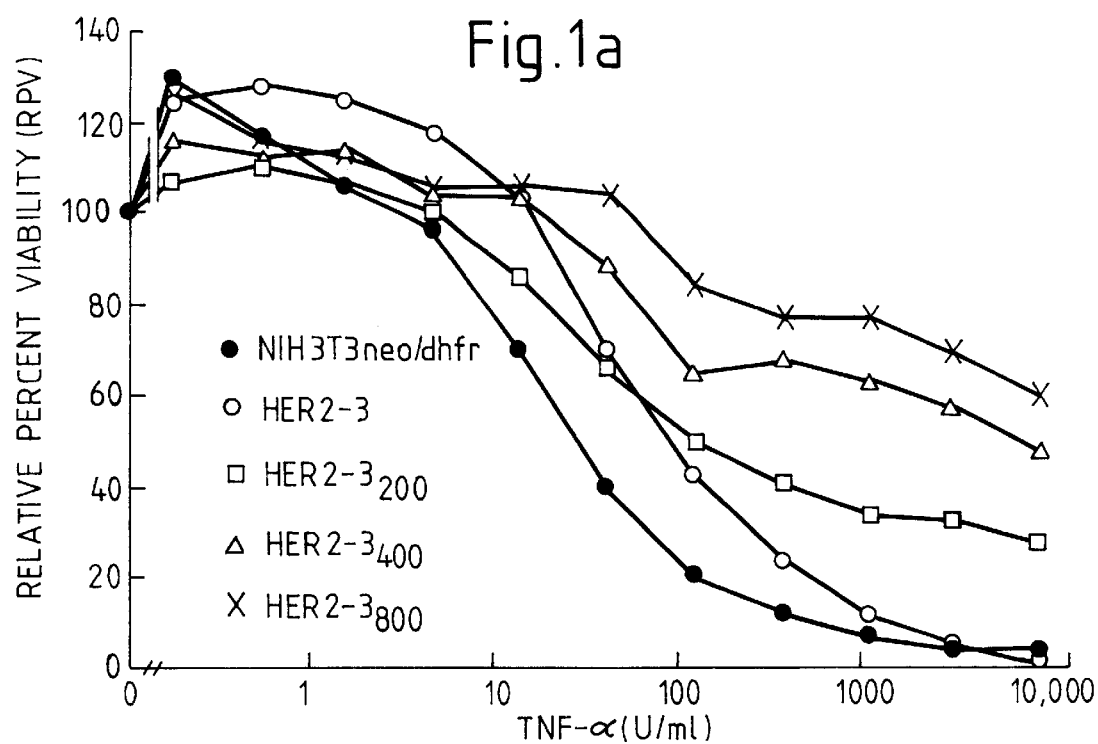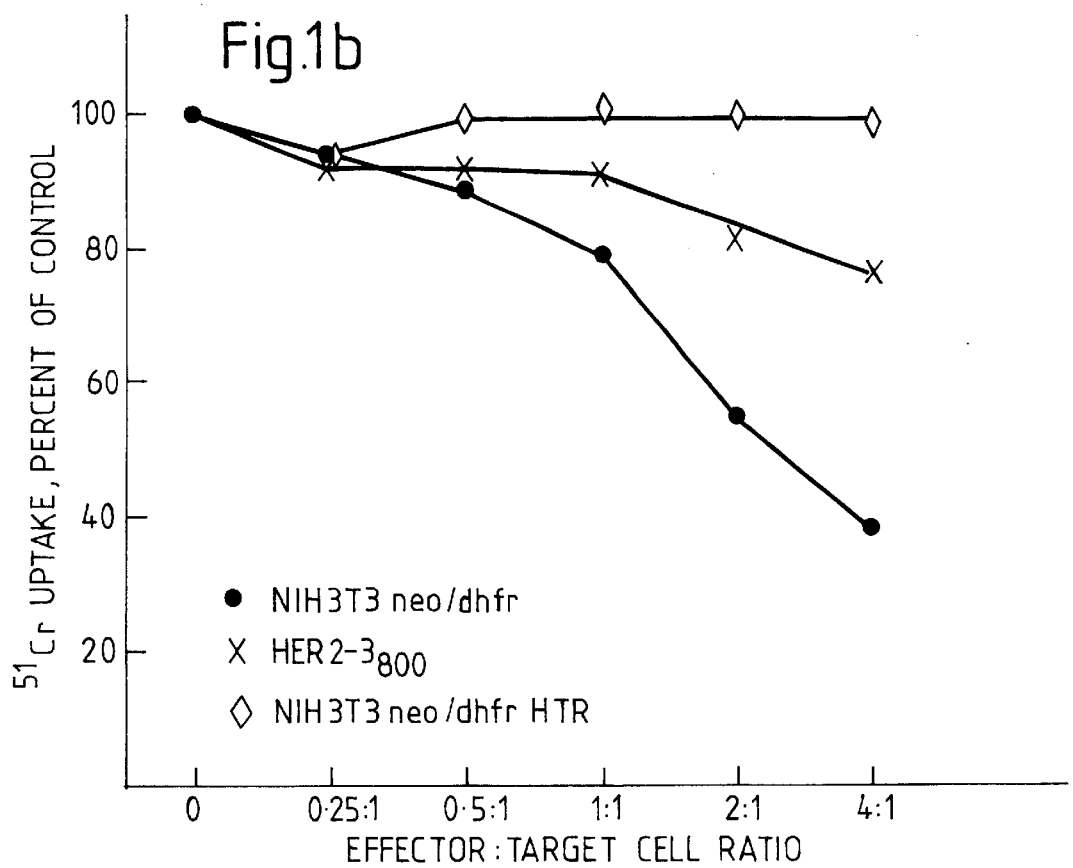

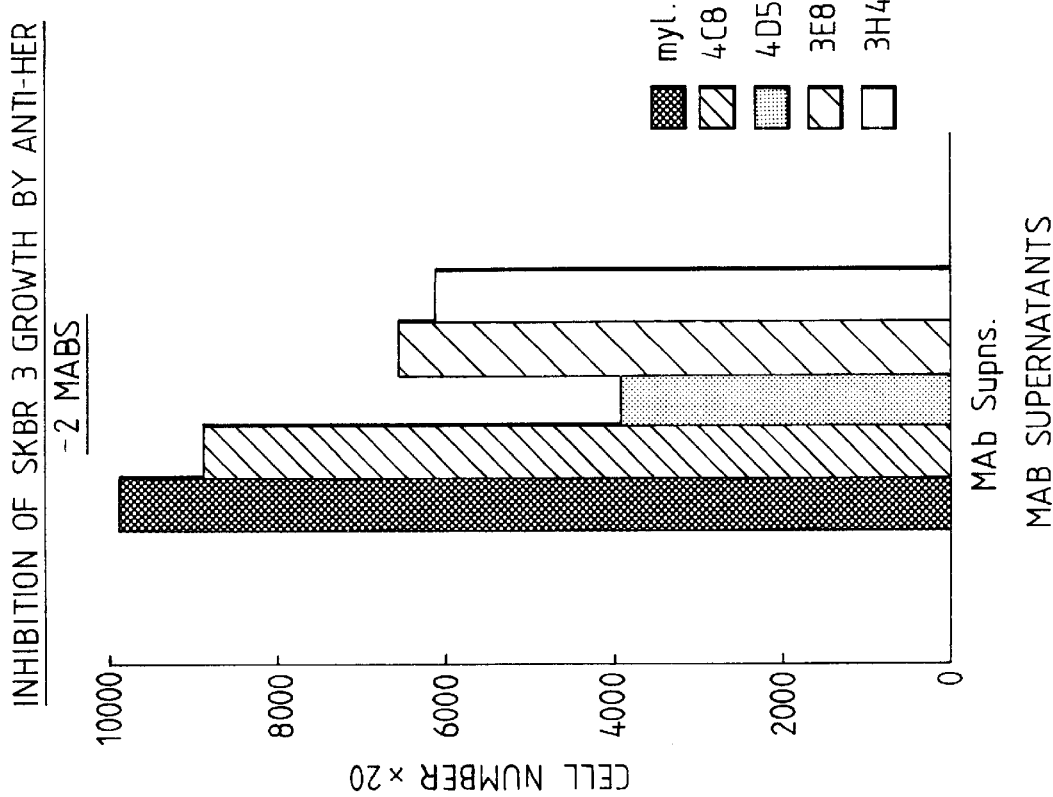
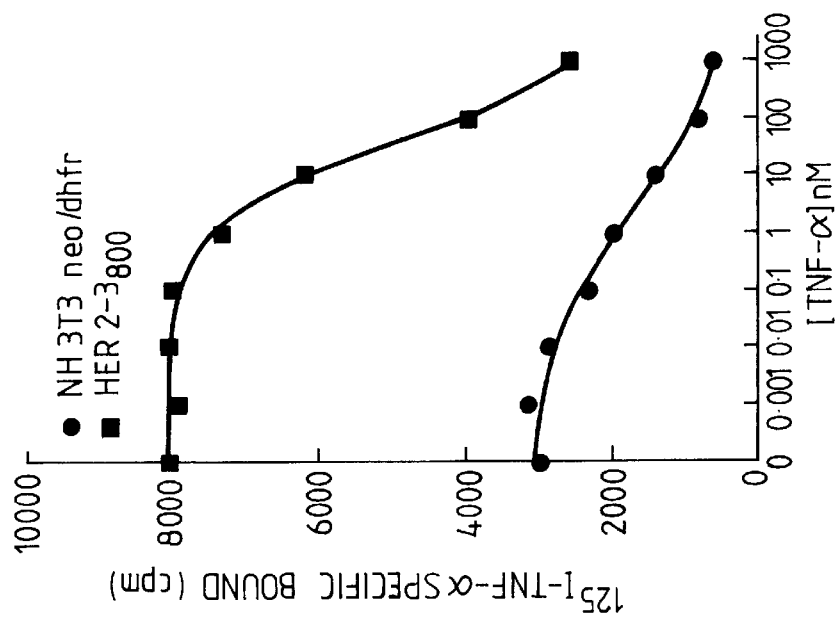

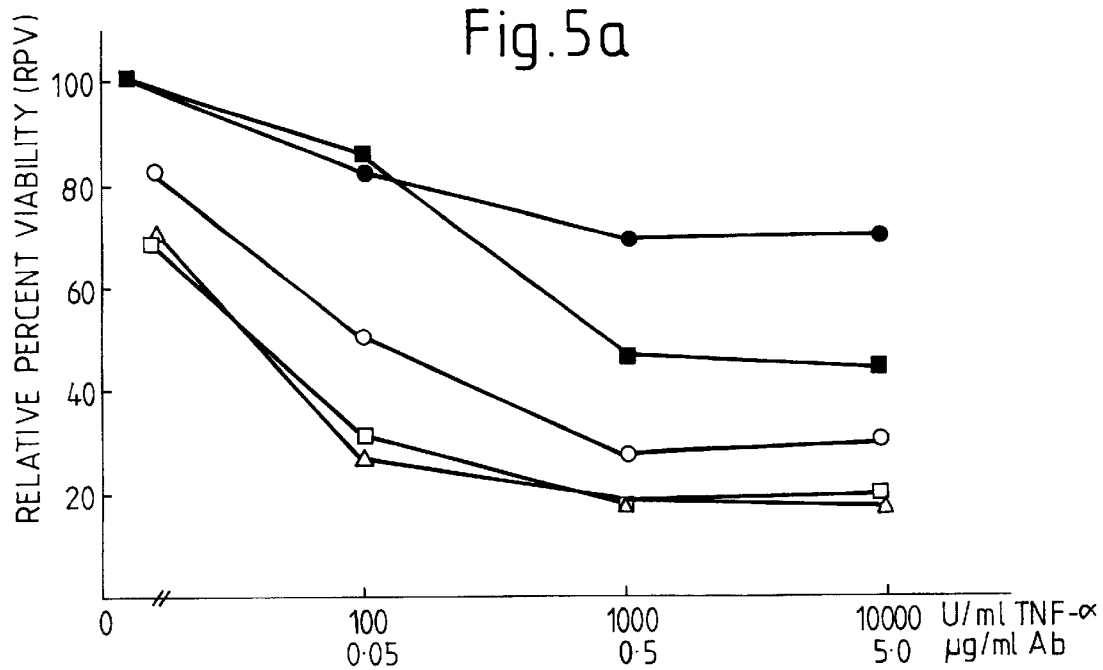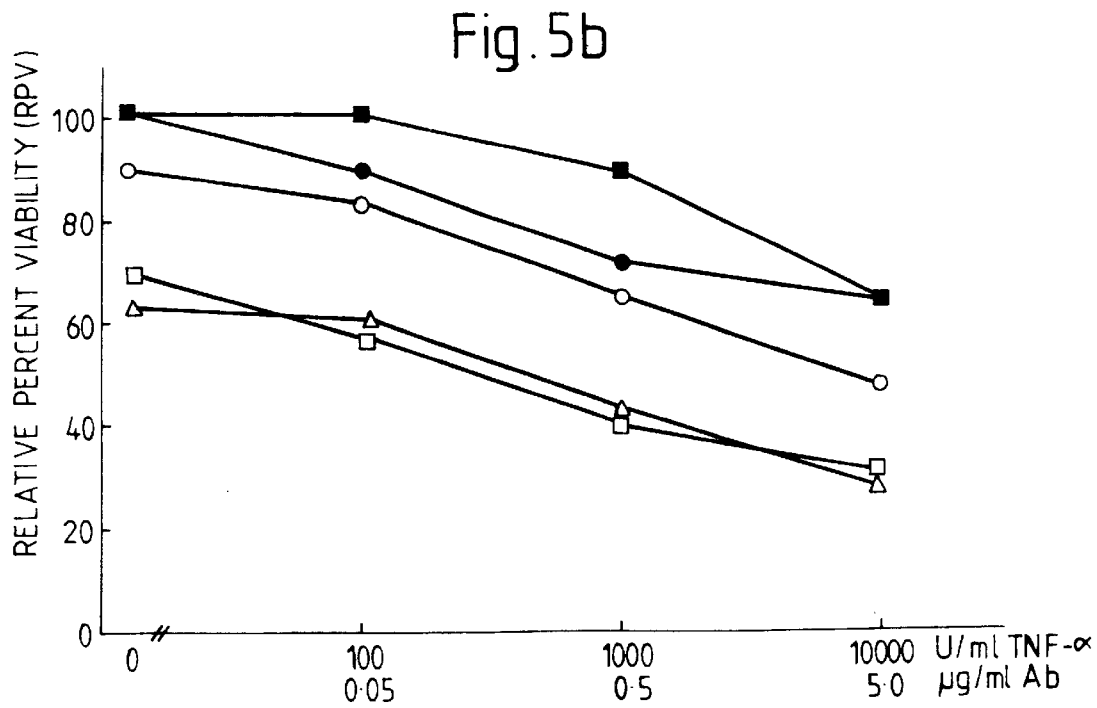

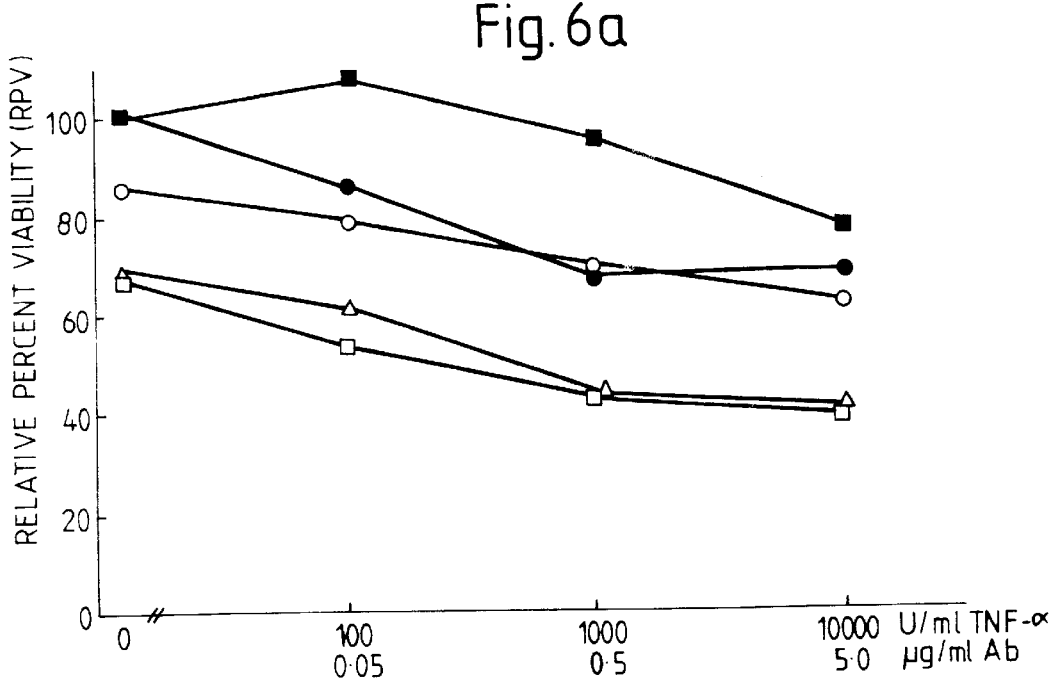
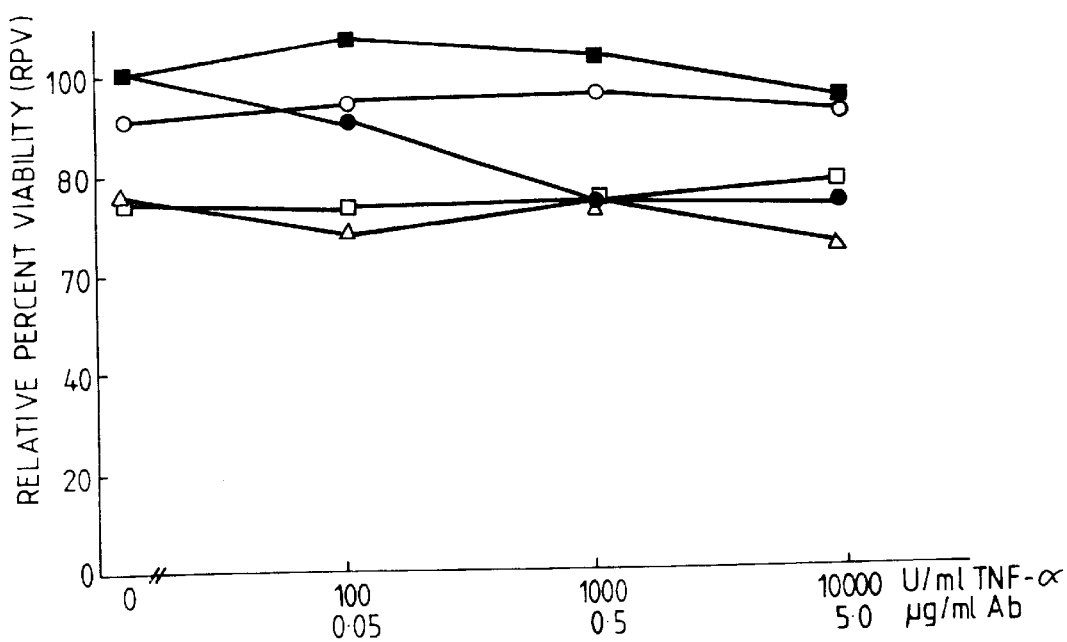

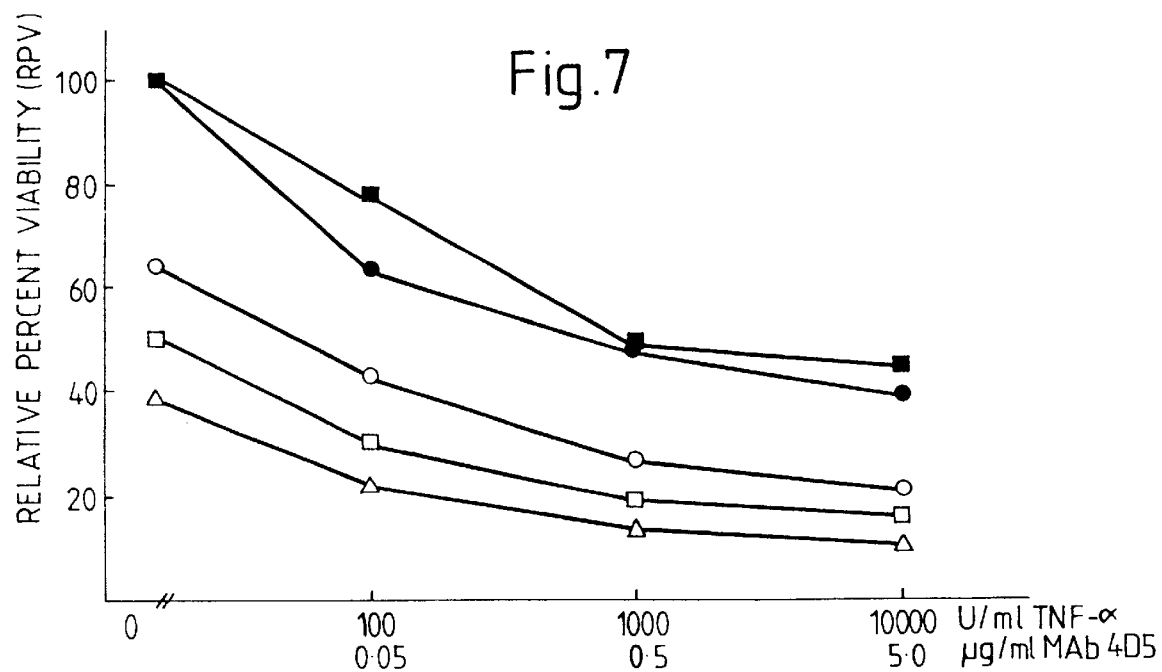
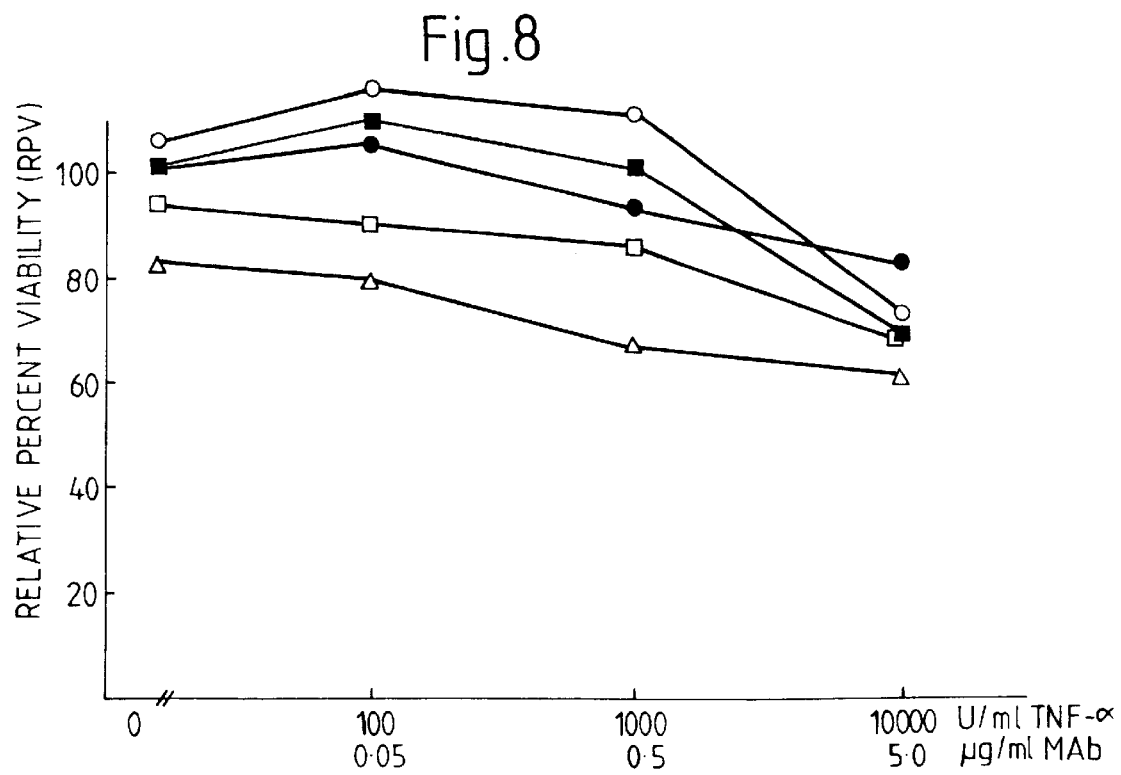

MONOCLONAL ANTIBODIES DIRECTED TO THE HER2 RECEPTOR

CROSS REFERENCES

This application is a continuation of U.S. application Ser. No. 09/044,197 filed Mar. 17, 1998, now U.S. Pat. No. 6,165,464 which is a continuation of U.S. application Ser. No. 08/447,478 filed May 23, 1995 (now U.S. Pat. No. 5,772,997 issued Jun. 30, 1998), which is a continuation of U.S. application Ser. No. 08/286,303 filed Aug. 5, 1994 (now U.S. Pat. No. 5,677,171 issued Oct. 14, 1997), which is a continuation of U.S. application Ser. No. 07/977,453 filed Nov. 18, 1992 (now abandoned), which is a continuation of U.S. application Ser. No. 07/147,461 filed Jan. 25. 1988 (now abandoned), which is a continuation-in-part of U.S. application Ser. No. 07/143,912 filed Jan. 12, 1988 (now abandoned), which applications are incorporated herein by reference and to which applications priority is claimed under 35 USC §120.

FIELD OF THE INVENTION

This invention is in the fields of immunology and cancer diagnosis and therapy. More particularly it concerns antibodies specifically binding growth factor receptors, hybridomas that produce these antibodies, immunochemicals made from the antibodies, and diagnostic methods that use the antibodies. The invention also relates to the use of the antibodies alone or in combination with cytotoxic factor(s) in therapeutic methods. Also encompassed by the invention is an assay for tyrosine kinases that are involved in tumorigenesis.

BACKGROUND OF THE INVENTION

Macrophages are one of the effector cell types that play an important role in immunosurveillance against neoplastic growth in vivo. In vitro, cell-mediated cytotoxicity requires selective binding between activated macrophages and target cells as well as the concomitant release of cytotoxic factors. Some of the cytotoxic factors secreted by activated macrophages include reactive oxygen species such as the superoxide anion and hydrogen peroxide, arginase, interleukin 1, and tumor necrosis factor-α (TNF-α). Acquired resistance to the toxic effects of these factors by tumor cells could be one mechanism which leads to the onset and spread of tumor formation in vivo.

The observation that TNF-α can act as a potent effector of the macrophage-mediated antitumor response provides a rationale for its use in further studies on the regulation of tumorigenesis in vivo and tumor cell growth in vitro. The genes encoding TNF-α and TNF-β, a structurally related cytotoxic protein formerly known as lymphotoxin, have been cloned and the corresponding proteins expressed in *Escherichia coli*. These proteins display an array of biological activities, including induction of hemorrhagic necrosis of Meth A sarcomas in vivo, inhibition of the growth of certain tumor cells in vitro, synergistic enhancement of the in vitro anticellular effects of IFN-γ, activation of human polymorphonuclear neutrophil functions, and inhibition of lipid biosynthesis. Recently, rHuTNF-α was shown to augment the growth of normal diploid fibroblasts in vitro. The divergent proliferative responses in the presence of rHuTNF-α are sometimes related to variations in TNF binding.

Growth factors and their receptors are involved in the regulation of cell proliferation and they also appear to play a key role in oncogenesis. Of the known proto-oncogenes, three are related to a growth factor or a growth factor receptor. These genes include c-sis, which is homologous to the transforming gene of the simian sarcoma virus and is the B chain of platelet-derived growth factor (PDGF); c-fms, which is homologous to the transforming gene of the feline sarcoma virus and is closely related to the macrophage colony-stimulating factor receptor (CSF-1R); and c-erbB, which encodes the EGF receptor (EGFR) and is homologous to the transforming gene of the avian erythroblastosis virus (v-erbB). The two receptor-related proto-oncogenes, c-fms and c-erbB, are members of the tyrosine-specific protein kinase family to which many proto-oncogenes belong.

Recently, a novel transforming gene was identified as a result of transfection studies with DNA from chemically induced rat neuroblastomas. This gene, called neu, was shown to be related to, but distinct from, the c-erbB proto-oncogene. By means of v-erbB and human EGFR as probes to screen human genomic and complementary DNA (cDNA) libraries, two other groups independently isolated human erbB-related genes that they called HER2 and c-erbB-2 respectively. Subsequent sequence analysis and chromosomal mapping studies revealed that c-erbB-2, and HER2 are species variants of neu. A fourth group, also using v-erbB as a probe, identified the same gene in a mammary carcinoma cell line, MAC 117, where it was found to be amplified five- to ten-fold.

This gene, which will be referred to herein as HER2, encodes a new member of the tyrosine kinase family; and is closely related to, but distinct from, the EGFR gene as reported by Coussens et al., *Science* 230, 1132 (1985). HER2 differs from EGFR in that it is found on band q21 of chromosome 17, as compared to band p11-p13 of chromosome 7, where the EGFR gene is located. Also, the HER2 gene generates a messenger RNA (MRNA) of 4.8 kb, which differs from the 5.8- and 10-kb transcripts for the EGFR gene. Finally, the protein encoded by the HER2 gene is 185,000 daltons, as compared to the 170,000-dalton protein encoded by the EGFR gene. Conversely, on the basis of sequence data, HER2 is more closely related to the EGFR gene than to other members of the tyrosine kinase family. Like the EGFR protein, the HER2 protein (p185) has an extracellular domain, a transmembrane domain that includes two cysteine-rich repeat clusters, and an intracellular kinase domain, indicating that it is likely to be a cellular receptor for an as yet unidentified ligand. HER2 p185 is referred to as p185 or the HER2 receptor herein.

Southern analysis of primary human tumors and established tumor-derived cell lines revealed amplification and in some cases rearrangement of the EGF receptor gene. Amplification was particularly apparent in squamous carcinomas and glioblastomas. The HER2 gene was also found to be amplified in a human salivary gland adenocarcinoma, a renal adenocarcinoma, a mammary gland carcinoma, and a gastric cancer cell line. Recently, Slamon et al., *Science* 235, 177 (1987) demonstrated that about 30% of primary human breast carcinoma tumors contained an amplified HER2 gene. Although a few sequence rearrangements were detected, in most tumors there were no obvious differences between amplified and normal HER2 genes. Furthermore, amplification of the HER2 gene correlated significantly with the negative prognosis of the disease and the probability of relapse.

To investigate the significance of the correlation between overexpression and cellular transformation as it has been observed for proto-oncogenes c-mos and N-myc, a HER2 expression vector and a selection scheme that permitted sequence amplification after transfection of mouse NIH 3T3 cells was employed by Hudziak et al., *Proc, Natl. Acad. Sci. (USA)* 84, 7159 (1987). Amplification of the unaltered HER2 gene in NIH 3T3 cells lead to overexpression of p185 as well as cellular transformation and tumor formation in athymic mice.

The effects of antibodies specifically binding growth factors or growth factor receptors has been studied. Examples are discussed below.

Rosenthal et al., *Cell* 46, 301 (1986) introduced a human TGF-α cDNA expression vector into established non-transformed rat fibroblast cells. Synthesis and secretion of TGF-α by these cells resulted in loss of anchorage-dependent growth and induced tumor formation in nude mice. Anti-human TGF-α monoclonal antibodies prevented the rat cells from forming colonies in soft agar, i.e. loss of anchorage dependence. Gill et al. in *J. Biol. Chem.* 259, 7755 (1984) disclose monoclonal antibodies specific for EGF receptor which were inhibitors of EGF binding and antagonists of EGF-stimulated tyrosine protein kinase activity.

Drebin et al. in *Cell* 41, 695 (1985) demonstrated that exposure of a neu-oncogene-transformed NIH 3T3 cell to monoclonal antibodies reactive with the neu gene product, cause the neu-transformed NIH 3T3 cell to revert to a non-transformed phenotype as determined by anchorage independent growth. Drebin et al. in *Proc. Natl. Acad. Sci.* 83, 9129 (1986) demonstrated that in vivo treatment with a monoclonal antibody (IgG2a isotype) specifically binding the protein encoded by the neu oncogene significantly inhibited the tumorigenic growth of neu-transformed NIH 3T3 cells implanted into nude mice.

Akiyama et al. in *Science* 232, 1644 (1986) raised antibodies against a synthetic peptide corresponding to 14 amino acid residues at the carboxy-terminus of the protein deduced from the c-erbB-2 (HER2) nucleotide sequence.

Growth factors have been reported to interact in both a synergistic and an antagonistic manner. For example, TGF-α and TGF-β synergistically enhance the growth of NRK-49F fibroblasts, whereas PDGF down regulates EGF receptor function on 3T3 cells. A variety of transformed cells secrete factors which are believed to stimulate growth by an autocrine mechanism. Sugarman et al., *Cancer Res.* 47, 780 (1987) demonstrated that under certain conditions, growth factors can block the antiproliferative effects of TNF-α on sensitive tumor cells. Specifically, epidermal growth factor (EGF) and recombinant human transforming growth factor-α (rHuTGF-α) were shown to interfere with the in vitro antiproliferative effects of recombinant human tumor necrosis factor-α (rHuTNF-α) and -β on a human cervical carcinoma cell line, ME-180. The inhibitory effect could be observed at EGF or rHuTGF-α concentrations of 0.1 to 100 ng/ml, and was maximal between 1 and 10 ng/ml. This response was apparently not due to down regulation of the TNF receptor or to alteration of the affinity of TNF-α for its receptor. Since the antiproliferative effect of recombinant human interferon-γ was not significantly affected by the presence of EGF or rHuTGF-α, the inhibition was specific for recombinant TNFs and was not due solely to enhanced proliferation induced by the growth factors. Neither growth factor had a substantial protective effect on the synergistic cytotoxicity observed when tumor cells were exposed simultaneously to rHuTNF-α and recombinant human interferon-γ. TGF-β can also interfere with the antiproliferative effects of rHuTNF-α in vitro. At concentrations of less than 1 ng/ml, TGF-β significantly antagonized the cytotoxic effects of rHuTNF-α on NIH 3T3 fibroblasts. Since EGF, platelet-derived growth factor, and TGF-β all enhanced NIH 3T3 cell proliferation, but only TGF-β interfered with rHuTNF-α cytotoxicity, the protective effects of TGF-β were not related in a simple manner to enhanced cell proliferation. rHuTGF-α and TGF-β did not have a significant protective effect against rHuTNF-α-mediated cytotoxicity on two other tumor cell lines, BT-20 and L-929 cells.

It is an object of the subject invention to provide antibodies capable of inhibiting growth factor receptor function.

It is a further object of the invention to provide an improved assay for the HER2 receptor.

It is a further object of the invention to provide improved methods of tumor therapy.

It is a further object of the invention to provide a method of inhibiting the growth of tumor cells which overexpress a growth factor receptor and/or growth factor.

It is a further object of the invention to provide a method for treating a tumor by treatment of the tumor cells with antibodies capable of inhibiting growth factor receptor function, and with cytotoxic factors such as tumor necrosis factor.

A still further object of the invention is to provide an assay for tyrosine kinases that may have a role in tumorigenesis.

Other objects, features and characterisitics of the present invention will become apparent upon consideration of the following description and the appended claims.

SUMMARY OF THE INVENTION

The subject invention relates to monoclonal antibodies specifically binding the external domain of the HER2 receptor. The invention also relates to an assay for the HER2 receptor comprising exposing cells to antibodies specifically binding the extracellular domain of the HER2 receptor, and determining the extent of binding of said antibodies to said cells. Another embodiment of the invention relates to a method of inhibiting growth of tumor cells by administering to a patient a therapeutically effective amount of antibodies capable of inhibiting the HER2 receptor function. A further embodiment of the invention relates to administering a therapeutically effective amount of antibodies capable of inhibiting growth factor receptor function, and a therapeutically effective amount of a cytotoxic factor. A still further embodiment of the invention is an assay for tyrosine kinases that may have a role in tumorigenesis comprising exposing cells suspected to be TNF-α resistant to TNF-α, isolating those cell which are TNF-α resistant, screening the isolated cells for increased tyrosine kinase activity, and isolating receptors and other proteins having increased tyrosine kinase activity.

BRIEF DESCRIPTION OF THE DRAWINGS

FIG. 1a shows TNF-α resistance of NIH 3T3 cells expressing various levels of HER2 p185. FIG. 1b shows macrophage cytotoxicity assays for NIH 3T3 cells expressing various levels of HER2 p185.

FIG. 2 demonstrates the level of TNF-α binding for a control cell line (NIH 3T3 neo/dhfr) and for a cell line overexpressing HER2 p185 (HER2-$3_{800}$).

FIG. 3 shows inhibition of SK BR3 cell growth by anti-HER2 monoclonal antibodies.

FIGS. 5a, 5b and 6a show percent viability of SK BR3 cells as a function of increasing TNF-α concentration and anti-HER2 p185 monoclonal antibody concentration. Each Figure shows the results for a different anti-HER2 p185 monoclonal antibody. FIG. 6b is a control using an irrelevant monoclonal antibody. In FIGS. 5a, 5b, 6a and 6b, ●—● represents TNF-α alone; ■—■ represents antibody (Ab) alone; ○—○ represents 100 U/ml TNF-α and ΔAb; □—□ represents 1000 U/ml TNF-α and ΔAb; and Δ—Δ represents 10,000 U/ml TNF-α and ΔAb.

FIG. 7 shoes percent viability of MDA-MB-175-VII cells as a function of increasing TNF-α concentration and anti-HER2 p185 monoclonal antibody concentration. In FIG. 7, ●—● represents TNF-α alone; ■—■ represents antibody (Ab) alone; ○—○ represents 100 U/ml TNF-α and ΔAb; □—□ represents 1000 U/ml TNF-α and ΔAb; and Δ—Δ represents 10,000 U/ml TNF-α and ΔAb.

FIG. 8 shows percent viability of NIH 3T3 cells overexpressing HER2 p185 as a function of increasing TNF-α concentration and anti-HER2 p185 monoclonal antibody concentration. In FIG. 8, ●—● represents TNF-α alone; ■—■ represents antibody (Ab) alone; ○—○ represents 100 U/ml TNF-α and ΔAb; □—□ represents 1000 U/ml TNF-α and ΔAb; and Δ—Δ represents 10,000 U/ml TNF-α and ΔAb.

DETAILED DESCRIPTION OF THE INVENTION

Figure 4:
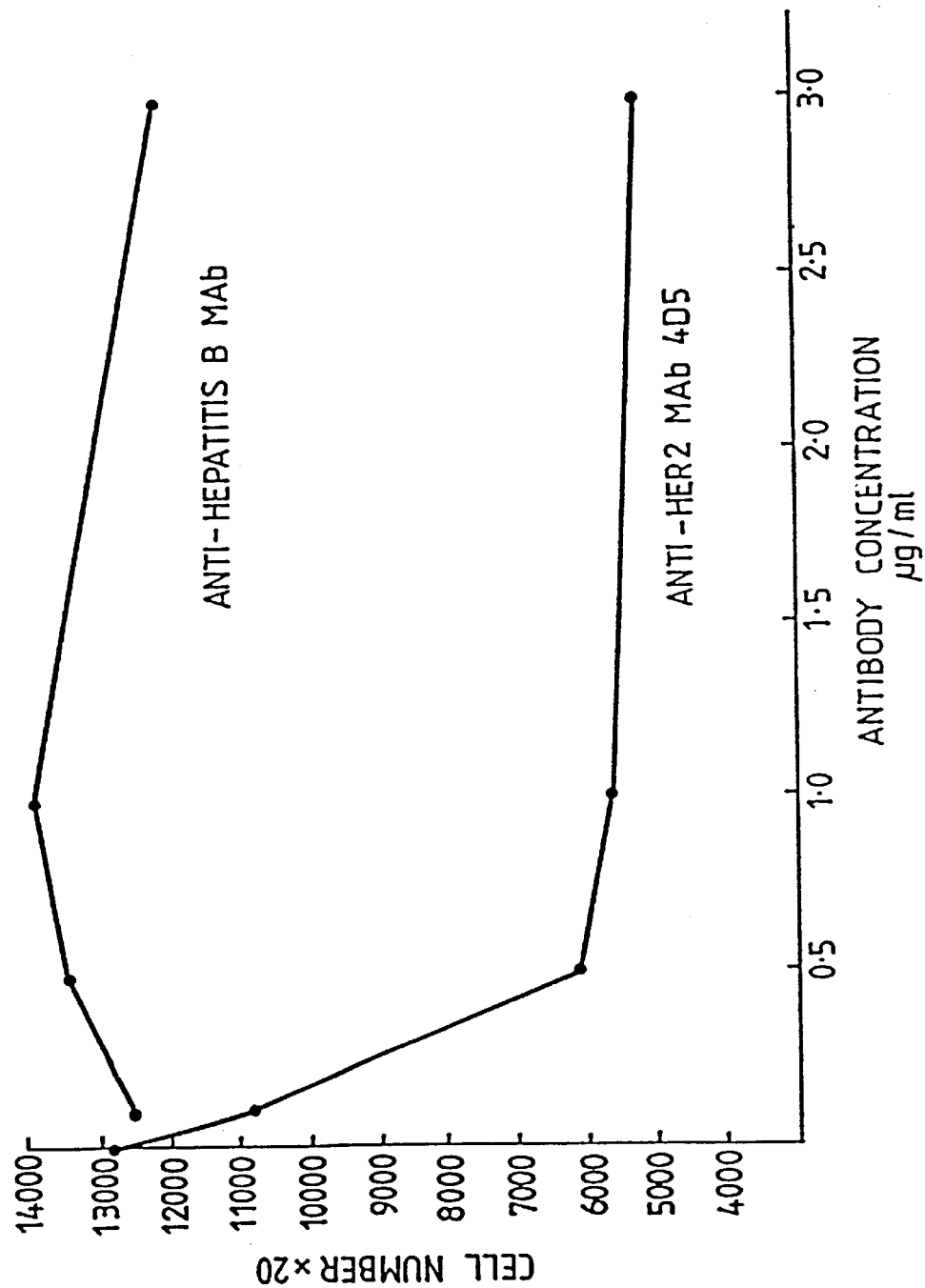
FIG. 4 is a dose response curve comparing the effect of an irrelevant monoclonal antibody (anti-HBV) and the effect of monoclonal antibody 4D5 (anti-HER2) on the growth of SK BR3 cells in serum.

A new application of antibodies to inhibit the growth of tumor cells has been discovered. Surprisingly it has been found that by inhibiting growth factor receptor function, e.g. the HER2 receptor function, cell growth is inhibited, and the cells are rendered more susceptible to cytotoxic factors. Thus, for example, breast cancer cells which are refractory to TNF-α alone can be made susceptible to TNF-α if the cells are first treated with antibodies which inhibit growth factor receptor function. The increase of susceptibility has been demonstrated using the HER2 receptor and monoclonal antibodies directed against the HER2 receptor, and tumor necrosis factor-α.

The method of this invention is useful in the therapy of malignant or benign tumors of mammals where the abnormal growth rate of the tumor is dependent upon growth factor receptors. Abnormal growth rate is a rate of growth which is in excess of that required for normal homeostasis and is in excess of that for normal tissues of the same origin. Many of these tumors are dependent upon extracellular sources of the growth factor recognized by the receptor, or upon synthesis of the growth factor by the tumor cell itself. This latter phenomenon is termed "autocrine" growth.

The methods of the subject invention is applicable where the following conditions are met:
(1) the growth factor receptor and/or ligand (growth factor) is expressed, and tumor cell growth depends upon the growth factor receptor biological function;
(2) antibodies specifically binding the growth factor receptor and/or ligand inhibit the growth factor receptor biological function.

While not wishing to be constrained to any particular theory of operation of the invention, it is believed that the antibodies inhibit growth factor receptor biological function in one or more of the following ways:
(a) The antibodies bind to the extracellular domain of the receptor and inhibit the ligand from binding the receptor;
(b) The antibodies bind the ligand (the growth factor) itself and inhibit the ligand from binding the receptor;
(c) The antibodies down regulate the growth factor receptor;
(d) The antibodies sensitize tumor cells to the cytotoxic effects of a cytotoxic factor such as TNF-α;
(e) The antibodies inhibit the tyrosine kinase activity of the receptor.

In cases (f) and (g), the antibodies inhibit growth factor receptor biological function indirectly by mediating cytotoxicity via a targeting function:
(f) The antibodies belong to a sub-class or isotype that upon complexing with the receptor activates serum complement and/or mediate antibody-dependent cellular cytotoxicity (ADCC), e.g. IgG2a antibodies;
(g) The antibodies which bind the receptor or growth factor are conjugated to a toxin (immunotoxins);

Advantageously antibodies are selected which greatly inhibit the receptor function by binding the steric vicinity of the ligand binding site of the receptor (blocking the receptor), and/or which bind the growth factor in such a way as to prevent (block) the ligand from binding to the receptor. These antibodies are selected using conventional in vitro assays for selecting antibodies which neutralize receptor function. Antibodies that act as ligand agonists by mimicking the ligand are discarded by conducting suitable assays as will be apparent to those skilled in the art. For certain tumor cells, the antibodies inhibit an autocrine growth cycle (i.e. where a cell secretes a growth factor which then binds to a receptor of the same cell). Since some ligands, e.g. TGF-α, are found lodged in cell membranes, the antibodies serving a targeting function are directed against the ligand and/or the receptor.

Certain tumor cells secrete growth factors that are required for normal cellular growth and division. These growth factors, however, can under some conditions stimulate unregulated growth of the tumor cell itself, as well as adjacent non-tumor cells, and can cause a tumor to form.

Epidermal Growth Factor (EGF) has dramatic stimulatory effects on cell growth. In purified receptor preparations, the EGF receptor is a protein kinase that is activated by the binding of EGF. Substrate proteins for this kinase are phosphorylated on tyrosine residues. The receptors for insulin, platelet-derived growth factor (PDGF) and other growth hormones also are tyrosine-specific kinases. It is believed that ligand binding to the receptor triggers phosphorylation of certain proteins by the receptor and in this way stimulates cell growth. About one-third of the known oncogenes encode proteins that phosphorylate tyrosine residues on other proteins. It is believed that these oncogene products trigger responses analogous to the responses of cells to growth factors and hormones. The erbB oncogene product is a portion of the EGF receptor that lacks the hormone-binding domain and may give rise to a constitutive growth-stimulating signal.

One embodiment of this invention is a method of inhibiting the growth of tumor cells by administering to a patient a therapeutically effective amount of antibodies that inhibit the HER2 receptor biological function of tumor cells.

Overexpression of growth factor receptors increases the resistance of cells to TNF as demonstrated below. Overexpression of the HER1 receptor (EGF receptor), met receptor-like protooncogene product, and HER2 receptor all show this increased resistance. It is shown in the Examples below that amplified expression of HER2, which encodes the HER2 receptor (p185), induces resistance of NIH 3T3 cells to the cytotoxic effects of macrophages or TNF-α. Induction of NIH 3T3 cell resistance to TNF-α by overexpression of p185 is accompanied by alterations in the binding of TNF-α to its receptor. Overexpression of p185 is also associated with resistance of certain human breast tumor cell lines to the cytotoxic effects of TNF-α.

In another embodiment of the invention, tumor cells are treated by (1) administering to a patient antibodies directed against the growth factor and/or its receptor, that inhibit the biological function of the receptor and that sensitize the cells to cytotoxic factors such as TNF, and (2) administering to the patient cytotoxic factor(s) or other biological response modifiers which activate immune system cells directly or indirectly to produce cytotoxic factors.

The cytotoxic factor, such as TNF-α, exerts its cytostatic (cell growth suppressive) and cytotoxic (cell destructive) effect. Examples of useful cytotoxic factors are TNF-α, TNF-β, IL-1, INF-γ and IL-2, and chemotherapeutic drugs such as 5FU, vinblastine, actinomycin D, etoposide, cisplatin, methotrexate, and doxorubicin. Cytotoxic factors can be administered alone or in combination. In a still further embodiment of the invention, the patient is treated with antibodies which inhibit receptor function, and with autologous transfer therapy, e.g. LAK or TIL cells.

Tumor necrosis factors are polypeptides produced by mitogen-stimulated macrophages or lymphocytes which are cytotoxic for certain malignantly transformed cells. The anti-tumor effect of TNF-α is known to be synergistically potentiated by interferons. The anti-tumor effect of TNF-α and TNF-β in admixture are additive, as are the antiviral effects of interferons alpha and beta.

The tumor necrosis factors include TNF-α and TNF-β. The former is described together with methods for its synthesis in recombinant cell culture, in U.S. Pat. No. 4,650,674, in copending U.S. Ser. No. 881,311, filed Jul. 2, 1986, and in European Patent Application 0168214; the latter is described in European Patent Application 0164965. Each of the documents is hereby incorporated by reference. The TNF-α and TNF-β described in these patent documents includes cytotoxic amino acid sequence and glycosylation variants. TNF-α and TNF-β from non-recombinant sources are also useful in the method of this invention.

The preferred TNF is mature human TNF-α from recombinant microbial cell culture. The TNF ordinarily will have a cytolytic activity on susceptible L-M murine cells of greater than about $1 \times 10^6$ units/mg, wherein a unit is defined as set forth in the above-described patent application.

In another embodiment of the subject invention, one or more additional cytokines and/or cytotoxic factors are administered with TNF-α, egs. interferons, interleukins, and chemotherapeutic drugs.

The compositions herein include a pharmaceutically acceptable vehicle, such as those heretofore used in the therapeutic administration of interferons or TNF, e.g. physiological saline or 5% dextrose, together with conventional stabilizers and/or excipients such as human serum albumin or mannitol. The compositions are provided lyophilized or in the form of sterile aqueous solutions.

Several variables will be taken into account by the ordinary artisan in determining the concentration of TNF in the therapeutic compositions and the dosages to be administered. Therapeutic variables also include the administration route, and the clinical condition of the patient.

The cytotoxic factor(s) and antibodies inhibiting growth factor receptor function are administered together or separately. If the latter, advantageously the antibodies are administered first and the TNF thereafter within 24 hours. It is within the scope of this invention to administer the TNF and antibodies in multiple cycles, depending upon the clinical response of the patient. The TNF and antibodies are administered by the same or separate routes, for example by intravenous, intranasal or intramuscular administration.

The method of the subject invention can be used with tumor cells which overexpress growth factor receptor and/or ligand where antibodies can be produced which inhibit the growth factor receptor function. A cell (e.g. breast tumor cell) overexpresses a growth factor receptor if the number of receptors on the cell exceeds the number on the normal healthy cell (e.g. normal breast tissue cell). Examples of carcinomas where the HER2 receptor is overexpressed (and thus the method of the subject invention is applicable), are human breast, renal, gastric and salivary gland carcinomas.

A further embodiment of the invention is an assay for identifying receptors and other proteins having increased tyrosine kinase activity, and for identifying oncogenes that transform cells. Amplification of certain oncogenes encoding tyrosine kinases correlates with TNF-α resistance. If cells are selected for resistance to TNF-α, some of these will have increased tyrosine kinase activity. Some of the tyrosine kinases will be receptors. The genes encoding the tyrosine kinases are then cloned using standard techniques for the cloning of genes. Identification of the receptor or other protein permits the design of reagents which inhibit receptor (or other protein) function and induce cellular sensitivity to cytotoxic factors as demonstrated herein with HER2. Identification of the receptor also permits subsequent identification of the receptor's ligand. The assay comprises exposing cells suspected to be TNF-α sensitive to TNF-α, and isolating those cells which are TNF-α resistant. The TNF-α resistant cells are then screened for increased tyrosine kinase activity, and receptors and other proteins having increased tyrosine kinase activity are isolated.

Antibodies

In accordance with this invention, monoclonal antibodies specifically binding growth factors or growth factor receptors such as the HER2 receptor, were isolated from continuous hybrid cell lines formed by the fusion of antigen-primed immune lymphocytes with myeloma cells. Advantageously, the monoclonal antibodies of the subject invention which bind growth factor receptors, bind the extracellular domain of the receptors. In another embodiment of the invention, polyclonal antibodies specifically binding the growth factors or growth factor receptors are used.

The antibodies of the subject invention which are used in tumor therapy advantageously inhibit tumor cell growth greater than 20%, and most advantageously greater than 50%, in vitro. These antibodies are obtained through screening (see, for example, the discussion relating to FIG. 3). The anti-HER2 receptor monoclonal antibodies of the subject invention which are used in tumor therapy are capable of inhibiting serum activation of the receptor.

Monoclonal antibodies are highly specific, being directed against a single antigenic site. Furthermore, in contrast to conventional antibody (polyclonal) preparations which typically include different antibodies directed against different determinants (epitopes), each monoclonal antibody is directed against a single determinant on the antigen. Monoclonal antibodies are useful to improve the selectivity and specificity of diagnostic and analytical assay methods using antigen-antibody binding. A second advantage of monoclonal antibodies is that they are synthesized by the hybridoma culture, uncontaminated by other immunoglobulins. Monoclonal antibodies may be prepared from supernatants of cultured hybridoma cells or from ascites induced by intra-peritoneal inoculation of hybridoma cells into mice.

The hybridoma technique described originally by Kohler and Milstein, *Eur. J. Immunol.* 6, 511 (1976) has been widely applied to produce hybrid cell lines that secrete high levels of monoclonal antibodies against many specific antigens.

The route and schedule of immunization of the host animal or cultured antibody-producing cells therefrom are generally in keeping with established and conventional techniques for antibody stimulation and production. Applicants have employed mice as the test model although it is contemplated that any mammalian subject including human subjects or antibody producing cells therefrom can be manipulated according to the processes of this invention to serve as the basis for production of mammalian, including human, hybrid cell lines.

After immunization, immune lymphoid cells are fused with myeloma cells to generate a hybrid cell line which can be cultivated and subcultivated indefinitely, to produce large quantities of monoclonal antibodies. For purposes of this invention, the immune lymphoid cells selected for fusion are lymphocytes and their normal differentiated progeny, taken either from lymph node tissue or spleen tissue from immunized animals. Applicants prefer to employ immune spleen cells, since they offer a more concentrated and convenient source of antibody producing cells with respect to the mouse system. The myeloma cells provide the basis for continuous propagation of the fused hybrid. Myeloma cells are tumor cells derived from plasma cells.

It is possible to fuse cells of one species with another. However, it is preferred that the source of immunized antibody producing cells and myeloma be from the same species.

The hybrid cell lines can be maintained in culture in vitro in cell culture media. The cell lines of this invention can be selected and/or maintained in a composition comprising the continuous cell line in the known hypoxanthine-aminopterin-thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody. The secreted antibody is recovered from tissue culture supernatant by conventional methods such as precipitation, ion exchange chromatography, affinity chromatography, or the like.

While the invention is demonstrated using mouse monoclonal antibodies, the invention is not so limited; in fact, human antibodies may be used and may prove to be preferable. Such antibodies can be obtained by using human hybridomas (Cole et al., *Monoclonal Antibodies and Cancer Therapy*, Alan R. Liss, p. 77 (1985)). In fact, according to the invention, techniques developed for the production of "chimeric antibodies" (Morrison et al., *Proc. Natl. Acad. Sci.* 81, 6851 (1984); Neuberger et al., *Nature* 312, 604 (1984); Takeda et al., *Nature* 314, 452 (1985)) by splicing the genes from a mouse antibody molecule of appropriate antigen specificity together with genes from a human antibody molecule of appropriate biological activity (such as ability to activate human complement and mediate ADCC) can be used; such antibodies are within the scope of this invention.

As another alternative to the cell fusion technique, EBV immortalized B cells are used to produce the monoclonal antibodies of the subject invention. Other methods for producing monoclonal antibodies such as recombinant DNA, are also contemplated.

The immunochemical derivatives of the antibodies of this invention that are of prime importance are (1) immunotoxins (conjugates of the antibody and a cytotoxic moiety) and (2) labeled (e.g. radiolabeled, enzyme-labeled, or fluorochrome-labeled) derivatives in which the label provides a means for identifying immune complexes that include the labeled antibody. The antibodies are also used to induce lysis through the natural complement process, and to interact with antibody dependent cytotoxic cells normally present.

Immunotoxins

The cytotoxic moiety of the immunotoxin may be a cytotoxic drug or an enzymatically active toxin of bacterial or plant origin, or an enzymatically active fragment ("A chain") of such a toxin. Enzymatically active toxins and fragments thereof used are diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolacca americana* proteins (PAPI, PAPII, and PAP-S), momordica charantia inhibitor, curcin, crotin, sapaonaria officinalis inhibitor, gelonin, mitogellin, restrictocin, phenomycin, and enomycin. In another embodiment, the antibodies are conjugated to small molecule anticancer drugs. Conjugates of the monoclonal antibody and such cytotoxic moieties are made using a variety of bifunctional protein coupling agents. Examples of such reagents are SPDP, IT, bifunctional derivatives of imidoesters such a dimethyl adipimidate HCl, active esters such as disuccinimidyl suberate, aldehydes such as glutaraldehyde, bis-azido compounds such as bis (p-azidobenzoyl) hexanediamine, bis-diazonium derivatives such as bis-(p-diazoniumbenzoyl)-ethylenediamine, diisocyanates such as tolylene 2,6-diisocyanate, and bis-active fluorine compounds such as 1,5-difluoro-2,4-dinitrobenzene. The lysing portion of a toxin may be joined to the Fab fragment of the antibodies.

Advantageously, monoclonal antibodies specifically binding the external domain of the target growth factor receptor, e.g. HER2 receptor, are conjugated to ricin A chain. Most advantageously the ricin A chain is deglycosylated and produced through recombinant means. An advantageous method of making the ricin immunotoxin is described in Vitetta et al., *Science* 238, 1098 (1987) hereby incorporated by reference.

When used to kill human cancer cells in vitro for diagnostic purposes, the conjugates will typically be added to the cell culture medium at a concentration of at least about 10 nM. The formulation and mode of administration for in vitro use are not critical. Aqueous formulations that are compatible with the culture or perfusion medium will normally be used. Cytotoxicity may be read by conventional techniques to determine the presence or degree of cancer.

Cytotoxic radiopharmaceuticals for treating cancer may be made by conjugating radioactive isotopes (e.g. I, Y, Pr) to the antibodies. The term "cytotoxic moiety" as used herein is intended to include such isotopes.

In another embodiment, liposomes are filled with a cytotoxic drug and the liposomes are coated with antibodies specifically binding a growth factor receptor. Since there are many receptor sites, this method permits delivery of large amounts of drug to the correct cell type.

Antibody Dependent Cellular Cytotoxicity

The present invention also involves a method based on the use of antibodies which are (a) directed against growth factor receptors such as HER2 p185, and (b) belong to a subclass or isotype that is capable of mediating the lysis of tumor cells to which the antibody molecule binds. More specifically, these antibodies should belong to a subclass or isotype that, upon complexing with growth factor receptors, activates serum complement and/or mediates antibody dependent cellular cytotoxicity (ADCC) by activating effector cells such as natural killer cells or macrophages.

The present invention is also directed to the use of these antibodies, in their native form, for therapy of human tumors. For example, many IgG2a and IgG3 mouse antibodies which bind tumor-associated cell surface antigens can be used in vivo for tumor therapy. In fact, since HER2 p185 is present on a variety of tumors, the subject antibodies and their therapeutic use have general applicability.

Biological activity of antibodies is known to be determined, to a large extent, by the Fc region of the antibody molecule (Uananue and Benacerraf, *Textbook of Immunology*, 2nd Edition, Williams & Wilkins, p. 218 (1984)). This includes their ability to activate complement and to mediate antibody-dependent cellular cytotoxicity (ADCC) as effected by leukocytes. Antibodies of different classes and subclasses differ in this respect, and, according to the present invention, antibodies of those classes having the desired biological activity are selected. For example, mouse immunoglobulins of the IgG3 and IgG2a class are capable of activating serum complement upon binding to the target cells which express the cognate antigen.

In general, antibodies of the IgG2a and IgG3 subclass and occasionally IgG1 can mediate ADCC, and antibodies of the IgG3, and IgG2a and IgM subclasses bind and activate serum complement. Complement activation generally requires the binding of at least two IgG molecules in close proximity on the target cell. However, the binding of only one IgM molecule activates serum complement.

The ability of any particular antibody to mediate lysis of the tumor cell target by complement activation and/or ADCC can be assayed. The tumor cells of interest are grown and labeled in vivo; the antibody is added to the tumor cell culture in combination with either serum complement or immune cells which may be activated by the antigen antibody complexes. Cytolysis of the target tumor cells is detected by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

Antibodies of virtually any origin can be used according to this embodiment of the present invention provided they bind growth factor receptors such as HER2 p185 and can activate complement or mediate ADCC. Monoclonal antibodies offer the advantage of a continuous, ample supply. In fact, by immunizing mice with, for example, HER2 p185, establishing hybridomas making antibodies to p185 and selecting hybridomas making antibodies which can lyse tumor cells in the presence of human complement, it is possible to rapidly establish a panel of antibodies capable of reacting with and lysing a large variety of human tumors.

Therapeutic Uses of the Antibodies

When used in vivo for therapy, the antibodies of the subject invention are administered to the patient in therapeutically effective amounts (i.e. amounts that eliminate or reduce the patient's tumor burden). They will normally be administered parenterally, when possible, at the target cell site, or intravenously. The dose and dosage regimen will depend upon the nature of the cancer (primary or metastatic), its population, the site to which the antibodies are to be directed, the characteristics of the particular immunotoxin (when used), e.g., its therapeutic index, the patient, and the patient's history. The amount of antibody administered will typically be in the range of about 0.1 to about 10 mg/kg of patient weight.

For parenteral administration the antibodies will be formulated in a unit dosage injectable form (solution, suspension, emulsion) in association with a pharmaceutically acceptable. parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate may also be used. Liposomes may be used as carriers. The vehicle may contain minor amounts of additives such as substances that enhance isotonicity and chemical stability, e.g., buffers and preservatives. The antibodies will typically be formulated in such vehicles at concentrations of about 1 mg/ml to 10 mg/ml.

The selection of an antibody subclass for therapy will depend upon the nature of the tumor antigen. For example, an IgM may be preferred in situations where the antigen is highly specific for the tumor target and rarely occurs on normal cells. However, where the tumor-associated antigen is also expressed in normal tissues, albeit at much lower levels, the IgG subclass may be preferred for the following reason: since the binding of at least two IgG molecules in close proximity is required to activate complement, less complement mediated damage may occur in the normal tissues which express smaller amounts of the antigen and, therefore, bind fewer IgG antibody molecules. Furthermore, IgG molecules by being smaller may be more able than IgM molecules to localize to tumor tissue.

There is evidence that complement activation in vivo leads to a variety of biological effects, including the induction of an inflammatory response and the activation of macrophages (Uananue and Benecerraf, *Textbook of Immunology*, 2nd Edition, Williams & Wilkins, p. 218 (1984)). Tumor cells are more sensitive to a cytolytic effect of activated macrophages than are normal cells, Fidler and Poste, *Springer Semin. Immunopathol.* 5, 161 (1982). The increased vasodilation accompanying inflammation may increase the ability of various anti-cancer agents, such as chemotherapeutic drugs, radiolabelled antibodies, etc., to localize in tumors. Therefore, antigen-antibody combinations of the type specified by this invention can be used therapeutically in many ways and may circumvent many of the problems normally caused by the heterogeneity of tumor cell populations. Additionally, purified antigens (Hakomori, *Ann. Rev. Immunol.* 2, 103 (1984)) or anti-idiotypic antibodies (Nepom et al., *Proc. Natl. Acad. Sci.* 81, 2864 (1985); Koprowski et al., *Proc. Natl. Acad. Sci.* 81, 216 (1984)) relating to such antigens could be used to induce an active immune response in human cancer patients. Such a response includes the formation of antibodies capable of activating human complement and mediating ADCC and by such mechanisms cause tumor destruction.

Immunoassays

Described herein are serological methods for determining the presence of HER2 p185. Essentially, the processes of this invention comprise incubating or otherwise exposing the sample to be tested to monoclonal antibodies and detecting the presence of a reaction product. Those skilled in the art will recognize that there are many variations of these basic procedures. These include, for example, RIA, ELISA, precipitation, agglutination, complement fixation and immuno-fluorescence. In the currently preferred procedures, the monoclonal antibodies are appropriately labeled.

The labels that are used in making labeled versions of the antibodies include moieties that may be detected directly, such as radiolabels and fluorochromes, as well as moieties, such as enzymes, that must be reacted or derivatized to be detected. The radiolabel can be detected by any of the currently available counting procedures. The preferred isotope labels are $^{99}$Tc, $^{14}$C, $^{131}$I, $^{125}$I, $^{3}$H, 32P and $^{35}$S. The enzyme label can be detected by any of the currently utilized colorimetric, spectrophotometric, fluorospectro-photometric or gasometric techniques. The enzyme is combined with the antibody with bridging molecules such as carbodiimides, periodate, diisocyanates, glutaraldehyde and the like. Many enzymes which can be used in these procedures are known and can be utilized. Examples are peroxidase, alkaline phosphatase, β-glucuronidase, β-D-glucosidase, β-D-galactosidase, urease, glucose oxidase plus peroxidase, galactose oxidase plus peroxidase and acid phosphatase. Fluorescent materials which may be used include, for example, fluorescein and its derivatives, rhodamine and its derivatives, auramine, dansyl, umbelliferone, luciferia, 2,3-dihydrophthalazinediones, horseradish peroxidase, alkaline phosphatase, lysozyme, and glucose-6-phosphate dehydrogenase. The antibodies may be tagged with such labels by known methods. For instance, coupling agents such as aldehydes, carbodiimides, dimaleimide, imidates, succinimides, bid-diazotized benzadine and the like may be used to tag the antibodies with the above-described fluorescent, chemiluminescent, and enzyme labels. Various labeling techniques are described in Morrison, *Methods in Enzymology* 32b, 103 (1974), Syvanen et al., *J. Biol. Chem.* 284, 3762 (1973) and Bolton and Hunter, *Biochem J.* 133, 529(1973) hereby incorporated by reference.

The antibodies and labeled antibodies may be used in a variety of immunoimaging or immunoassay procedures to detect the presence of cancer in a patient or monitor the status of such cancer in a patient already diagnosed to have it. When used to monitor the status of a cancer, a quantitative immunoassay procedure must be used. If such monitoring assays are carried out periodically and the results compared, a determination may be made regarding whether the patient's tumor burden has increased or decreased. Common assay techniques that may be used include direct and indirect assays. If the sample includes cancer cells, the labeled antibody will bind to those cells. After washing the tissue or cells to remove unbound labeled antibody, the tissue sample is read for the presence of labeled immune complexes. In indirect assays the tissue or cell sample is incubated with unlabeled monoclonal antibody. The sample is then treated with a labeled antibody against the monoclonal antibody (e.g., a labeled antimurine antibody), washed, and read for the presence of ternary complexes.

For diagnostic use the antibodies will typically be distributed in kit form. These kits will typically comprise: the antibody in labeled or unlabeled form in suitable containers, reagents for the incubations for an indirect assay, and substrates or derivatizing agents depending on the nature of the label. HER2 p185 controls and instructions may also be included.

The following examples are offered to more fully illustrate the invention, but are not to be construed as limiting the scope thereof.

Experimental

Amplified Expression of p185$^{HER2}$ and Tyrosine Kinase Activity

A series of NIH 3T3 cell lines expressing various levels of p185 were constructed as disclosed in Hudziak et al., *Proc. Natl. Acad. Sci.* (USA) 84, 7159 (1987), hereby incorporated by reference. The parental cell line had a nontransformed, TNF-α-sensitive phenotype. The control cell line (NIH 3T3 neo/dhfr) was prepared by transfection with pCVN, an expression plasmid encoding neomycin resistance as a selectable marker, and dihydrofolate reductase (which encodes methotrexate resistance and which permits amplification of associated DNA sequences).

pCVN-HER2 (which encodes, in addition, the entire 1255 amino acid p185 receptor-like tyrosine kinase under the transcriptional control of the RSV-LTR) was introduced into NIH 3T3 cells in a parallel transfection. Transfectants were selected by resistance to the aminoglycoside antibiotic G418. The pCVN-HER2 primary transfectants (HER2-3) do not have a transformed morphology and fail to grow in soft agar. Stepwise amplification of HER2 expression by selection in 200 nM (HER2-3$_{200}$), 400 nM (HER2-3$_{400}$), and 800 nM (HER2-3$_{800}$) methotrexate, however, results in transformation as judged by morphological criteria, the ability to grow in soft agar, and the ability to form tumors in nude mice.

The amplification of expression of p185 was documented by immunoprecipitation from cells that were metabolically labeled with $^{35}$S-methionine. The tyrosine kinase activity associated with p185 in these cell lines was measured by autophosphorylation in vitro. For an autoradiograph of $^{35}$S-methionine labeled p185, 200 μCi of $^{35}$S-methionine (Amersham; 1132 Ci/mmol) was added to 1.5 ml of methionine-free labeling medium, containing 2% dialyzed fetal bovine serum. 1.0×10$^6$ cells of each type were counted by Coulter counter, plated in 60 mm culture dishes (Falcon), and allowed to adhere for 12 h. Following an 8 h labeling period the cells were lysed and the HER2-encoded p185 was analyzed. For an autoradiograph of self-phosphorylated HER2-receptor tyrosine kinase, the p185 was immunoprecipitated and the pellet was resuspended in 50 μl of tyrosine kinase reaction buffer. The samples were incubated at 4° C. for 20 min. The self-phosphorylated p185 from the various cell lines was then visualized by autoradiography following gel electrophoresis. The molecular weight markers used were myosin (200 kD) and β-galactosidase (116 kD). The results showed that expression of p185 and its associated tyrosine kinase increased in parallel during amplification. Quantitative densitometry of the in vitro autophosphorylation reactions showed that the tyrosine kinase activity increased at least 5 to 6-fold between HER2-3 and HER2-3$_{200}$ and between HER2-3$_{200}$ and HER2-3$_{400}$, while only a small difference was observed between HER2-3$_{400}$ and HER2-3$_{800}$ (see the Tyrosine Kinase column of Table 1 below).

Relative amounts of tyrosine kinase present in each of the cell types of Table 1 were determined by taking ratios of the areas under the curves obtained by scanning autoradiograms (using an LKB2202 laser densitometer). The autoradiograms had been exposed for various times to allow for linearity in the determinations, and then normalized by comparison to the HER2 primary transfectant (HER2-3).

Resistance to TNF-α

The cell lines described above were then tested for sensitivity to TNF-α and macrophage-induced cytotoxicity.

In FIG. 1a, TNF-α resistance of the control cells and the HER2-transfected NIH 3T3 cells is shown. Cells were seeded into 96-well microtiter plates at a density of 5,000 cells/well in DMEM supplemented with 10% calf serum, 2mM L-glutamine, 100 U/ml penicillin and 100 μg/ml streptomycin. The cells were allowed to adhere for 4 hrs before the addition of a range of concentrations of TNF-α. Specific activity of the TNF-α (recombinant human TNF-α) was 5×10$^7$ U/mg as determined in an L-M cell cytotoxicity assay in the presence of actinomycin D. After incubation at 37° C. for 72 hr, the monolayers were washed with PBS and stained with crystal violet dye for determination of relative cell viability. These measurements were repeated six times. Results from a representative experiment are shown in FIG. 1a.

In FIG. 1b, macrophage-mediated cytotoxicity assays are shown. TNF-α resistant cells (neo/dhfr HTR) were derived by subculturing a clone of NIH 3T3 neo/dhfr in media containing 10,000 U/ml TNF-α. For macrophage cytotoxicity assays, NIH 3T3 neo/dhfr, HER2-3$_{800}$ and neo/dhfr HTR cells were seeded into 96-well microtiter plates as in 1a above. Human macrophages were obtained as adherent cells from peripheral blood of healthy donors. Adherent cells were scraped and resuspended in media, activated for 4 hr. with 10 μg/ml E. coli-derived lipopolysaccharide (LPS; Sigma) and 100 U/ml of recombinant human interferon-gamma (rHuIFN-γ, Genentech, Inc.). The cell suspension was then centrifuged for 10 minutes at 1200 rpm and the resulting pellet was washed with media to remove the LPS and rHuIFN-γ. The macrophages were resuspended in media, counted, and then added to the target cells to obtain the desired effector to target ratios. After a 72 hr incubation at 37° C., the monolayers were washed with media and $^5$Cr was added to each well for determination of viability by $^{51}$Cr uptake.

TABLE 1

Correlation between HER2-associated tyrosine kinase levels and resistance to TNF-α

| Cell Type | Percent Viability | Tyrosine Kinase |
|---|---|---|
| 1. NIH 3T3 neo/dhfr | 3.6 ± 0.6 | * |
| 2. NIH 3T3 neo/dhfr$_{400}$ | 8.3 ± 1.0 | * |
| 3. HER2-3 | 2.0 ± 0.4 | 1.0 |
| 4. HER2-3$_{200}$ | 27.5 ± 2.7 | 6.73 |
| 5. HER2-3$_{400}$ | 48.4 ± 1.4 | 32.48 |
| 6. HER2-3$_{800}$ | 58.7 ± 1.3 | 39.61 |
| 7. BT-20 | 1.6 ± 0.3 | <0.1 |
| 8. MCF7 | 2.5 ± 0.3 | 0.26 |
| 9. MDA-MB-361 | 26.8 ± 6.6 | 10.65 |
| 10. MDA-MB-175-VII | 31.2 ± 4.4 | 0.9 |
| 11. SK-BR-3 | 56.4 ± 5.5 | 31.0 |
| 12. MDA-MB-231 | 64.2 ± 9.3 | <0.1 |

* not measured

Percent viability is given at $1.0 \times 10^4$ cytotoxicity units per ml of TNF-α. The breast tumor cell lines were obtained from the ATCC and maintained in DMEM supplemented with 10% fetal bovine serum, 2 mM glutamine, 100 U/ml penicillin and 100 μg/ml streptomycin.

As shown in FIG. 1a and Table 1, stepwise amplification of HER2 receptor expression resulted in a parallel induction of resistance to TNF-α. The primary transfectants (HER2-3), which do not have a transformed phenotype, demonstrated little increased resistance. However, the transformed lines HER2-3$_{200}$, HER2-3$_{400}$ and HER2-3$_{800}$ do show a stepwise loss in sensitivity to TNF-α-mediated cytotoxicity as compared to NIH 3T3 neo/dhfr (FIG. 1a and Table 1), although the MDA-MB-175-VII cells had elevated p185 expression compared to the TNF-α sensitive BT20 and MCF7 cell lines. In correlation with the levels of p185 expression (Table 1), the difference in sensitivity of HER2-3$_{200}$ and HER2-3$_{400}$ (27.5% vs. 48.4% viability at $1 \times 10^4$ U/ml TNF-α) is greater than the difference between HER2-3$_{400}$ and HER2-3$_{800}$ (48.4% vs. 58.7% viability, see FIG. 1a and Table 1). A similar result was obtained when NIH 3T3 neo/dhfr and HER2-3$_{800}$ were compared for sensitivity to activated macrophages (FIG. 1b). These data suggest that amplification of the expression of HER2 induces resistance to TNF-α, and also show that this correlates with resistance to an important component of the early host defense mechanism, the activated macrophage. Amplification of the control plasmid (pCVN) in the cell line NIH 3T3 neo/dhfr$_{400}$ did not induce increased resistance to TNF-α (Table 1). This demonstrates that neither gene transfection or gene amplification, per se, has any effect on the sensitivity of cells to TNF-α.

The observation that NIH 3T3 cell lines expressing high levels of p185 were resistant to cytotoxicity induced by TNF-α or macrophages suggested that this may be one mechanism leading to tumor development. To test this possibility six breast tumor cell lines were screened for amplification of HER2 and sensitivity to TNF-α-mediated cytotoxicity. The results (Table 1) demonstrated that sensitivity to growth inhibition by TNF-α is inversely correlated with the expression of HER2-associated tyrosine kinase measured in vitro autophosphorylation assay for BT-20, MCF7, MDA-MB-361 and SK-BR-3. Two of the TNF-α-resistant breast tumor cell lines (MDA-MB-175-VII and MDA-MB-231), however, had no demonstrable amplified expression of HER2 as compared to the HER2-3 control (Table 1), although the MDA-MB-175-VII cells had elevated p185 expression compared to the TNF-α sensitive BT20 and MCF7 cell lines. These results are consistent with previous reports of the frequency of HER2 amplification in primary breast tumors and tumor-derived cell lines, and suggest the existence of other cellular mechanisms which may lead to TNF-α resistance.

Experiments also showed that overexpression of the EGF receptor, and cellular transformation by the src oncogene, correlates with resistance to TNF-α.

TNF-α Receptor Binding

In order to investigate whether the TNF-α receptor was altered in HER2-3$_{800}$, as opposed to NIH 3T3 neo/dhfr, the binding of $^{125}$I-labeled TNF-α was compared between these cell lines. FIG. 2 shows a TNF-α receptor binding analysis. Displacement curves show binding of $^{125}$I-TNF-α to NIH 3T3 neo/dhfr and HER2-$_{380}$. Competition binding assays were performed. Briefly, a suspension of $2.0 \times 10^6$ cells were incubated in a final volume of 0.5 ml of RPMI-1640 medium containing 10% fetal bovine serum. Binding of $^{125}$I-TNF-α ($0.2 \times 10^6$ cpm) to the cells was determined in the presence or absence of varying concentrations of unlabeled TNF-α at 4° C. under saturation equilibrium conditions. Each data point represents the mean of triplicate determinations. After incubation overnight, cells were washed twice with incubation buffer and cell bound radioactivity was determined. Non-specific binding was <10% of total binding.

The results showed a 2-3 fold increase in total specific binding for HER2-3$_{800}$ as compared to NIH 3T3 neo/dhfr (FIG. 2). In addition, the displacement curve for binding on HER2-3$_{800}$ is also shifted toward lower affinity binding as compared to NIH 3T3 neo/dhfr (FIG. 2).

Production of Anti-HER2 Monoclonal Antibodies

Five female Balb/c mice were immunized with HER2 amplified NIH 3T3 transformed cells over a period of 22 weeks. The first four injections each had approximately $10^7$ cells/mouse. They were administered intraperitoneally in half a milliliter of PBS on weeks 0, 2, 5, 7. Injections five and six were with a wheat germ agglutinin partially purified membrane preparation which had a whole protein concentration of about 700 μg/ml. A 100 μl/injection was administered to each mouse intraperitoneally on weeks 9 and 13. The last injection was also with the purified material but was administered three days prior to the date of fusion intravenously.

Bleeds from the mice were tested at various times in a radioimmunoprecipitation using whole cell lysates. The three mice with the highest antibody titers were sacrificed and spleens were fused with the mouse myeloma cell line X63-Ag8.653 using the general procedure of Mishell & Shiigi, *Selected Methods in Cellular Immunology*, W. H. Freeman & Co., San Francisco, p. 357–363 (1980) with the following exceptions. Cells were plated at a density of approximately $2 \times 10^5$ cells/well into ten 96 well microtiter plates. Hybrids were selected using hypoxanthine-azoserine rather than hypoxanthine-aminoptern-thymidine (HAT).

Hybridoma supernatants were tested for presence of antibodies specific for HER2 receptor by ELISA and radioimmunoprecipitation.

For the ELISA, 3.5 µg/ml of the HER2 receptor (purified on the wheat germ agglutinin column) in PBS was adsorbed to immulon II microtiter plates overnight at 4° C. or for 2 hours at room temperature. Plates were then washed with phosphate buffered saline with 0.05% Tween 20 (PBS-TW20) to remove unbound antigen. Remaining binding sites were then blocked with 200 µl per well of 1% bovine serum albumin (BSA) in PBS-TW20 and incubated 1 hour at room temperature. Plates were washed as above and 100 µl of hybridoma supernatant was added to each well and incubated for 1 hour at room temperature. Plates were washed again and 100 µl per well of an appropriate dilution of goat anti-mouse immunoglobulin coupled to horseradish peroxidase was added. The plates were incubated again for 1 hour at room temperature and then washed as above. O-phenylene diamine was added as substrate, incubated for 15–20 minutes at room temperature and then the reaction was stopped with 2.5 M $H_2SO_4$. The absorbance of each well was then read at 492 nm.

For the radioimmunoprecipitation, first the wheat germ purified HER2 rceptor preparation was autophosphorylated in the following manner: a kinase solution with the following final concentrations was made: 0.18 mCi/ml $\gamma P^{32}$-ATP (Amersham), 0.4 mM $MgCl_2$, 0.2 mM $MnCl_2$, 10 µM ATP, 35 µg/ml total protein concentration of partially purified HER2 all diluted in 20 mM Hepes, 0.1% triton 10% glycerol buffer (HTG). This reaction was incubated for 30 minutes at room temperature. 50 µl hybridoma supernatant was then added to 50 µl of the kinase reaction and incubated 1 hour at room temperature. 50 µl of goat anti-mouse IgC precoated protein-A sepharose CL4B, at a sepharose concentration of 80 mg/ml, was added to each sample and incubated 1 hour at room temperature. The resulting immunocomplexes were then washed by centrifugation twice with HTG buffer and finally with 0.2% deoxycholate 0.2% Tween 20 in PBS, in a microfuge and aspirated between washes. Reducing sample buffer was added to each sample and samples were heated at 95° C. for 2–5 minutes, insoluble material was removed by centrifugation and the reduced immunocomplex was loaded onto a 7.5% polyacrylamide gel containing SDS. The gel was run at 30 amp constant current and an autoradiograph was obtained from the finished gel.

Approximately 5% of the total well supernatants reacted with the HER2 receptor in the ELISA and/or radioimmunoprecipitation. From this initial 5% (about 100), some hybrids produced low affinity antibodies and others suffered from instability and stopped secreting antibodies leaving a total of 10 high affinity stable HER2 specific antibody producing cell lines. These were expanded and cloned by limiting dilution (Oi, V.T. and Herzenberg, L.A., "Immunoglobulin Producing Hybrid Cell Lines" in *Selected Methods in Cellular Immunology*, p. 351–372 Mishell, B. B. and Shiigi, S. M. (eds.), W. H. Freeman and Co. (1980)). Large quantities of specific monoclonal antibodies were produced by injection of cloned hybridoma cells in pristaned primed mice to produce ascitic tumors. Ascites were then collected and purified over a protein-A sepharose column.

Screening of Antibodies

The 10 high affinity monoclonal antibodies were then screened in a number of assays for anti-transformation or anti-tumor cell activity. Monoclonal antibodies were selected on the basis of growth inhibiting activity against the human tumor line SK BR3 which is derived from a breast tumor and contains an amplified HER2 gene and overexpresses the HER2 p185 tyrosine kinase. The initial screen used conditioned medium (medium in which the cells were grown for several days containing any secreted products of the cells including antibodies produced by the cells) from the hybridoma cell lines.

SK BR3 cells were plated at 20,000 cells/35 mm dish. Either conditioned medium from the hybridoma parent line (producing everything but anti-HER2 monoclonals) as a control, or the anti-HER2 monoclonals were added. After 6 days, the total number of SK BR3 cells were counted using an electronic Coulter cell counter. Cells were grown in a 1:1 mixture of F-12 and DMEM supplemented with 10% fetal bovine serum, glutamine, and penicillin-streptomycin. The volume per plate was 2 mls/35 mm dish. 0.2 mls of myeloma conditioned medium was added per 35 mm dish. Each control or anti-HER2 MAb was assayed in duplicate and the two counts averaged.

The result of the survey is shown in FIG. 3. Monoclonal antibody 4D5 (ATCC CRL 10463, deposited with American Type Culture Collection,10801 University Blvd., Manassas, Va. 20110-2209 under the Budapest Treaty on May 24, 1990) markedly inhibited the growth of the breast tumor line SK BR3. Other anti-HER2 antibodies inhibited growth to a significant but lesser extent (egs., MAbs 3E8 and 3H4). Still other anti-HER2, antibodies (not shown) did not inhibit growth.

A repeat experiment using purified antibody rather than hybridoma conditioned medium confirmed the results of FIG. 3. FIG. 4 is a dose response curve comparing the effect of an irrelevant monoclonal antibody (anti-HBV) and monoclonal antibody 4D5 (anti-HER2) on the growth of the SK BR3 cell line in 10% fetal bovine serum.

Down Regulation of the HER2 Receptor

The SK BR3 cells were pulse labeled with 100 uci $^{35}$S-methionine for 12 hours in methionine-free medium. Then either an irrelevant (anti-Hepatitis B surface antigen) or anti-HER2 MAb (4D5) was added to the cells at 5 µg/ml. After 11 hours, the cells were lysed and HER2 p185 immunoprecipitates and the proteins were analyzed by a 7.5% acrylamide gel followed by autoradiography. The SDS-PAGE gel of the $^{35}$S-methionine labeled HER2 p185 from SK BR3 cells demonstrated that the HER2 levels are down-regulated by MAb 4D5.

Treatment of Breast Tumor Cells with Monoclonal Antibodies and TNF-α

SK-BR-3 breast tumor cells were seeded at a density of $4 \times 10^4$ cells per well in 96-well microtiter plates and allowed to adhere for 2 hours. The cells were then treated with different concentrations of anti-HER2 monoclonal antibody (MAb) 4D5 or irrelevant isotype matched (anti-rHuIFN-γ MAb) at 0.05, 0.5 or 5.0 µg/ml for 4 hours prior to the addition of 100, 1,000 or 10,000 U/ml rHuTNF-α. After a 72 hour incubation, the cell monolayers were stained with crystal violet dye for determination of relative percent viability (RPV) compared to control (untreated) cells. Each treatment group consisted of 6 replicates. The results are shown in FIGS. 5 and 6. These Figures show that incubation of cells overexpressing HER2 receptor with antibodies directed to the extracellular domain of the receptor induce sensitivity to the cytotoxic effects of TNF-α. Equivalent treatment of breast tumor cells MDA-MB-175 VII gave similar results (see FIG. 7). Treatment of human fetal lung fibroblasts (WI-38) with MAb resulted in no growth inhibition or induction of sensitivity to TNF-α as expected.

Treatment of NIH 3T3 Cells Overexpressing HER2 p185 with Monoclonal Antibodies and TNF-α

NIH 3T3 HER2-3$_{400}$ cells were treated with different concentrations of anti-HER2 MAbs as in the above described treatment of SK-BR3 cells. The results for MAb 4D5 are shown in FIG. 8. The results indicate that cells other than of breast tumor cell lines which overexpress the HER2 receptor are growth inhibited by antibodies to the HER2 receptor, and senstivity to TNF-α is induced in the presence of these antibodies.

In Vivo Treatment of NIH 3T3 Cells Overexpressing HER2 with Anti-HER2 IgG2A Monoclonal Antibodies NIH 3T3 cells transfected with either a HER2 expression plasmid (NIH 3T3$_{400}$) or the neo-DHFR vector were injected into nu/nu (athymic) mice subcutaneously at a dose of $10^6$ cells in 0.1 ml of phosphate-buffered saline. On days 0, 1, 5 and every 4 days thereafter, 100 μg (0.1 ml in PBS) of either an irrelevant or anti-HER2 monoclonal antibody of the IgG2A subclass was injected intraperitoneally. Tumor occurence and size were monitored for the 1 month period of treatment.

TABLE 2

| Group # | Cell Line | Treatment | # Tumors/ # Animals | Tumor Size of Survivors: Length x Width Average in mm$^2$ at 31 Days |
|---|---|---|---|---|
| 1 | HER2 (3T3$_{400}$) | Irrelevant MAb (anti-Hepatitis B Virus) | 6/6 | 401 |
| 2 | HER2 (3T3$_{400}$) | 2H11 anti-HER2 | 2/6 | 139 |
| 3 | HER2 (3T3$_{400}$) | 3E8 anti-HER2 | 0/6 | 0 |
| 4 | neo/DHFR | None | 0/6 | 0 |

Table 2 shows that the 2H11 MAb has some anti-tumor activity (MAb 2H11 has very slight growth inhibiting properties when screened against tumor line SK BR3) and the 3E8 MAb gives 100% tumor growth inhibition during the course of the experiment.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. A method of inhibiting the growth of tumor cells that overexpress HER2 receptor comprising administering to a patient an antibody comprising an antigen binding region which specifically binds to an extracellular domain of the HER2 receptor in an amount effective to inhibit growth of the tumor cells in the patient, wherein the antibody is not conjugated to a cytotoxic moiety.

2. A method of treating cancer that overexpresses HER2 receptor comprising administering to a patient an antibody comprising an antigen binding region which specifically binds to an extracellular domain of the HER2 receptor in an amount effective to eliminate or reduce the patient's tumor burden, wherein the antibody is not conjugated to a cytotoxic moiety.

3. The method of claim 2 wherein the patient has breast cancer.

4. A method of treating renal cancer that overexpresses HER2 receptor comprising administering to a patient an antibody comprising an antigen binding region which specifically binds to an extracellular domain of the HER2 receptor in an amount effective to eliminate or reduce the patient's tumor burden.

5. A method of treating gastric cancer that overexpresses HER2 receptor comprising administering to a patient an antibody comprising an antigen binding region which specifically binds to an extracellular domain of the HER2 receptor in an amount effective to eliminate or reduce the patient's tumor burden.

6. A method of treating salivary gland cancer that overexpresses HER2 receptor comprising administering to a patient an antibody comprising an antigen binding region which specifically binds to an extracellular domain of the HER2 receptor in an amount effective to eliminate or reduce the patient's tumor burden.

7. A method of treating cancer comprising identifying a patient with cancer characterized by amplification of the HER2 gene and/or overexpression of the HER2 receptor and administering to the patient thus identified an antibody comprising an antigen binding region which specifically binds to an extracellular domain of the HER2 receptor in an amount effective to inhibit growth of the cancer of the patient.

8. A method of treating cancer that overexpresses HER2 receptor comprising administering to a patient an effective amount of an antibody comprising an antigen binding region which specifically binds to an extracellular domain of the HER2 receptor and an effective amount of a cytokine, wherein administration of the antibody and the cytokine to the patient inhibits growth of the cancer in the patient.

9. The method of claim 8 wherein the cytokine is tumor necrosis factor-α (TNF-α).

10. The method of claim 8 wherein the cytokine is tumor necrosis factorβ (TNF-β).

11. The method of claim 8 wherein the cytokine is interleukin-1 (IL-1).

12. The method of claim 8 wherein the cytokine is interleukin-2 (IL-2).

13. The method of claim 8 wherein the cytokine is interferon-γ (IFN-γ).

14. The method of claim 8 wherein the antibody and cytokine are administered to the patient together.

15. The method of claim 8 wherein the antibody and cytokine are administered to the patient separately.

16. The method of claim 8 wherein the antibody binds to the HER2 receptor epitope to which antibody 4D5 (ATCC CRL 10463) binds.

17. The method of claim 8 wherein the antibody has the identifying biological characteristics of antibody 4D5 (ATCC CRL 10463).

18. The method of claim 8 wherein the antibody interacts with antibody dependent cytotoxic cells.

* * * * *